US008541551B2

(12) United States Patent
Rodriguez et al.

(10) Patent No.: US 8,541,551 B2
(45) Date of Patent: Sep. 24, 2013

(54) IMMUNOGEN AND ANTIVENOM AGAINST VIOLIN SPIDER VENOM

(75) Inventors: Alejandro Olvera Rodriguez, Morelos (MX); Roberto Pablo Stock Silberman, Morelos (MX); Blanca Margarita Ramos Cerrillo, Mexico City (MX); Rosana Sanchez-Lopez, Morelos (MX); Alejandro Alagon Cano, Morelos (MX)

(73) Assignees: Universidad Nacional Autonoma de Mexico, Mexico City (MX); Laboratorios Silanes S.A. de C.V., Mexico City (MX)

( * ) Notice: Subject to any disclaimer, the term of this patent is extended or adjusted under 35 U.S.C. 154(b) by 0 days.

(21) Appl. No.: 13/610,516

(22) Filed: Sep. 11, 2012

(65) Prior Publication Data

US 2013/0071399 A1    Mar. 21, 2013

Related U.S. Application Data

(63) Continuation of application No. 11/574,488, filed as application No. PCT/MX2005/000071 on Aug. 29, 2005, now Pat. No. 8,287,860.

(30) Foreign Application Priority Data

Aug. 31, 2004    (MX) .................... PA/a/2004/008435

(51) Int. Cl.
*A61K 38/43*    (2006.01)
*C07K 14/435*    (2006.01)
*C12N 9/16*    (2006.01)

(52) U.S. Cl.
USPC ...................... 530/350; 424/185.1; 424/236.1

(58) Field of Classification Search
None
See application file for complete search history.

(56) References Cited

U.S. PATENT DOCUMENTS

| 5,443,976 | A | 8/1995 | Carroll |
| 5,904,922 | A | 5/1999 | Carroll |
| 8,287,860 | B2 * | 10/2012 | Rodriguez et al. ......... 424/130.1 |
| 2011/0177078 | A1 * | 7/2011 | Rodriguez et al. ......... 424/139.1 |

FOREIGN PATENT DOCUMENTS

EP    1247816    10/2002

OTHER PUBLICATIONS

Ramos-Cerrillo et al., Toxicon 44: 507-514, Oct. 2004.*
Barbaro K C et al., "Compared chemical properties of dermonecrotic and lethal toxins from spiders of the genus *Loxosceles (Araneae)*". J. Protein Chem. May 1996; vol. 15, No. 4, pp. 337-343.
Tambourgi D V et al., "Molecular cloning, expression, function and immunoreactivities of members of a gene family of phingomyelinases from *Loxosceles* venom". Molecular Immunology Jul. 2004; vol. 41, No. 8, pp. 831-840.
Pedrosa M D et al., "Molecular cloning and expression of a functional dermonecrotic and haemolytic factor from *Loxosceles laeta* venom". Biochemical and biophysical research communications. Nov. 15, 2002, vol. 298, No. 5, pp. 638-645.
Kalapothakis E et al., "Molecular cloning, expression an immunological properties of LiD1, a protein from the dermonecrotic family of *Loxosceles intermedia* spider venom". Toxicon. Dic 2002. vol. 40, No. 12, pp. 1691-1699.
Ramos-Cerrillo B et al., "Genetic and enzymatic characterization of sphingomyelinase D isoforms from the North American fiddleback spiders *Loxosceles boneti* and *Loxosceles reclusa*". TOXICON. Oct. 2004; vol. 44, pp. 507-514.
Witkowski et al, Biochemistry 38(36): 11643-50, Sep. 7, 1999.
Seffernick et al, J Bacteriol 183 (8): 2405-10, Apr. 2001.
Beckwith et al, Toxicon 18: 663-666, 1980.
Tol et al, N Engl J Med. 360(6):563-72, Feb. 5, 2009.
Harlow et al, in Antibodies a Laboratory Manual, 1988, Cold Spring harbor laboratory publication, Cold Spring Harbor, NY, pp. 626-629.

* cited by examiner

*Primary Examiner* — Phuong Huynh
(74) *Attorney, Agent, or Firm* — Reinhart Boerner Van Deuren P.C.

(57) ABSTRACT

The invention relates to the isolation, characterization and expression of DNA fragments encoding sphingomyelinases D from three species of *Loxosceles* genus spiders, namely *L. boneti., L. reclusa* and *L. laeta*, and the toxoids thereof. The invention also relates to the production of active sphingomyelinases D and the toxoids thereof using recombinant means and to the use of same as an immunogen for the production in vertebrates of antibodies that neutralize the corresponding venom and the respective fragments F(ab')2. The invention further relates to the use of recombinant sphingomyelinases D as part of an antigen matrix which can be used in the immunopurification of antibodies and the fragments thereof or as part of any diagnostic device used to obtain clinical confirmation that the causal agent of poisoning in a patient is a spider of the *Loxosceles* genus. In addition, the invention includes molecular vectors for the expression of the DNA fragments, strains comprising same, which can express *Loxosceles sphingomyelinases* D, and methods for the express thereof.

6 Claims, 5 Drawing Sheets

Figure 4

Percent of amino acid identity in necrotoxins of different Loxosceles species

| species | Lb1 | Lr1 | Lr2 | La | Li | LI-H17 | LI-H13 | LI-1 | LI-2 |
|---|---|---|---|---|---|---|---|---|---|
| Lb1 | - | | | | | | | | |
| Lr1 | 91 | - | | | | | | | |
| Lr2 | 84 | 90 | - | | | | | | |
| La | 86 | 88 | 87 | - | | | | | |
| Li | 82 | 84 | 85 | 80 | - | | | | |
| LI-H17 | 57 | 60 | 60 | 59 | 59 | - | | | |
| LI-H13 | 57 | 60 | 61 | 58 | 60 | 80 | - | | |
| LI-1 | 56 | 59 | 59 | 58 | 59 | 99 | 80 | - | |
| LI-2 | 57 | 60 | 61 | 59 | 59 | 82 | 94 | 82 | - |

Figure 5

IMMUNOGEN AND ANTIVENOM AGAINST VIOLIN SPIDER VENOM

CROSS-REFERENCE TO RELATED PATENT APPLICATIONS

This patent application is a continuation of U.S. patent application Ser. No. 11/574,488, filed Oct. 12, 2007, which is now U.S. Pat. No. 8,287,860 and claims the benefit of PCT/MX2005/000071 filed Aug. 29, 2005, and co-pending PA/a/2004/008435 filed Aug. 31, 2004, the entire teachings and disclosure of which are incorporated herein by reference thereto.

TECHNICAL FIELD

This invention refers to the recombinant proteins that comprise the sequence of sphingomyelinase D, the main component of the venom of the violin spider (*Loxosceles boneti*; *Loxosceles reclusa*, and *Loxosceles laeta* [Peruvian variety]). When they are injected into mammals, the proteins generate an effective immune response to neutralize the toxic action of the whole venom of those arachnids. It also refers to the use of these proteins as immunogens for the production in vertebrates of antibodies against the whole venoms of said arachnids. It also refers to the composition of said antibodies or the antigen-binding fragments thereof and their use for the treatment of violin spider bite poisoning, and to an antigenic matrix capable of specifically binding neutralizing antibodies of the arachnid's venom, useful for the purification by immunoaffinity of such sero-therapic and fab-therapic agents. Additionally, it refers to a diagnostic, device that incorporates said matrix to determine the species of the spider causing the poisoning, and to the method for performing said diagnosis. In another scope of the invention, the DNA fragments that codify the respective recombinant proteins and the expression constructions for said fragments, as well as the bacterial cells transformed with said constructions and the method for producing the proteins using recombinant means are also included.

BACKGROUND

Spiders pertaining to the *Loxosceles* genus are commonly known as violin spiders because they have a violin-shaped mark with the neck pointing backwards in the anterosuperior part of the cephalothorax (Platnick, 2000).

Spiders of this genus are found all over the world, generally in tropical and temperate climate regions (Ramos, 2000). In Mexico, there are about 39 species of this genus (Hoffman, 1976; Gerstch, 1983). In their natural habitat, they can be found under the bark of trees, under rocks and in caves. They can be found in coexistence with human beings: under furniture, in the corners of rooms, in cracks, grooves of livestock facilities, wood, bricks, and abandoned waste. One of the main causes for *Loxosceles* bite accidents is, precisely, the constant coexistence with man.

Poisoning caused by the bite of spiders of the *Loxosceles* genus is called LOXOSCELISM. The violin spider bite commonly produces local necrotic lesions or dermonecrosis (necrotic Loxoscelism), while in some cases it can cause non-necrotizing systemic effects (systemic Loxoscelism).

The extent of local necrosis is related to the spider's stage in of development, the dose of venom injected in the bite and the immune state of the patient (Moye de Alba, 1997; Maguire, 1998).

Dermonecrosis is preceded by edema, the accumulation of inflammatory cells and vasodilatation, all of which culminates in a black vesicle commonly called "bull's eye" lesion. Sometimes the *Loxosceles* genus may also produce intravascular hemolysis associated with spherocytosis, a condition that persists for several days (Maguire, 1988; Rosse, 1998).

In Mexico, 15 cases of violin spider bite poisoning were treated in the Social Security institute (personal information, Dr. Maria del Carmen Sánchez. "La Raza" Hospital, Mexico City) during the past 5 years, 11 in adults and 4 in children. In 53.3% of the cases, in addition to the necrotic loxoscelism, there was systemic loxoscelism, and 62% of the cases where both occurred, the patients died.

Biochemistry of the Venom

Until now, few spider venoms have been studied in detail. The *Loxosceles* venom is composed of at least ten to twelve components (Russell, 1987), among them: sterases, alkaline phosphatase, hyaluronidase, phosphohydrolases, lypases and proteases, among others. It has so far been proven that the main component, and the one that causes dermonecrosis, is sphingomyelinase D (SMD). This enzyme binds to the cell membranes (epithelial, endothelial of the vascular tissue and red blood cells) hydrolyzing sphingolipids to subsequently release phosphoceramide and choline (Gatt, 1978). The hydrolysis induces the chemotaxis of neutrophils causing vascular thrombosis and an Arthus-Type reaction (Moye de Alba, 1997; Maguire, 1998; Sánchez, 1993).

Hyaluronidase, other enzymes involved in poisoning, are common in the poisons of almost all spiders (Tan and Ponnundarai, 1992). They have been detected in a considerable number of species (Geren, 1984) including *Loxosceles* sp., although in these last species, very low enzymatic activity has been reported (Wright, 1973). Hyaluronidases are considered venom-dispersion factors, because the hydrolysis of the hyaluronic acid facilitates the diffusion of the other toxic components within the victim's tissues (Cevallos et al., 1992). Hyaluronidases act as a dispersing agent and it is thought that proteases might be directly involved in dermonecrosis through the digestion of the proteins that form the extracellular matrix (Young, 2001).

Recent studies have identified two proteases, Loxolysine A and Loxolysine B, in *L. intermedia*. Loxolysine A is a 20-28 kDa metalloprotease with fibrogenolytic activity (degrading fibrinogen) and fibronectinolytic activity (degrading fibronectin). This protein might be involved in the local hemorrhagic effects observed at the site of the bite and in some cases in the systemic hemorrhages, while Loxolysine B is a 32-35 kDa protease with gelatinolytic activity, and although its function is as yet unknown, it may possibly participate in the degradation of collagen within the extracellular matrix (Feitosa et al., 1998).

Three isoforms (P1, P2, and P3) of the necrotoxic fraction have been found in *L. intermedia*; they were extremely similar to each other at the biochemical and immunological level. The first two are necrotoxic, P2 with a greater effect, while P3 was completely inactive. The analysis of the amino acidic sequences of the first 35 amino acids of the extreme amino terminus of the isoforms revealed that they were identical in many ways. They were also compared with the partial sequences of the toxins of other previously reported *Loxosceles* species, obtaining a high degree of similarity (Tambourgi, 1998).

In 1968 Smith and Micks demonstrated that the injection of *L. reclusa*, *L. laeta* or *L. rufuscens* venom into rabbits produced similar necrotic reactions. Recent studies compared the amino terminus sequences of sphingomyelinase of *L.*

*reclusa, L, deserta, L. gaucho, L. intermedia* and *L. laeta* venom determining that they were homologous among them (Barbara et al., 1996B).

To date, the complete sequences of the sphingomyelinase D of only 2 of the *Loxosceles* species have been reported—*L. Laeta* (Fernandes Pedrosa et al., 2002) and *L. intermedia* (Kalapothakis et al., 2002); they show an identity of barely 59% between them. Only the first 34 AAs of the sphingomyelinase of *L. reclusa* are known and they happen to have an 85.7% similarity with the equivalent sequence of *L. intermedia* and 60% with that of *L. laeta*; for this reason it is impossible to establish a probable sequence for the almost 244 AAs of the enzyme that are still unknown. Similarly, only 35 AAs of the amino terminus region of the sphingomyelinase D of *L. deserta* and 39 of that of *L. gaucho* are known (for *L. deserta* only the sequence derived from the gene is known).

Work on the generation of antibodies against particular species of *Loxosceles* and cross tests of the same with venoms of spiders of other species of this genus have been reported. For example, a set of monoclonal antibodies against the dermonecrotic component (of 35 K da) of the venom of *L. gaucho* was developed, which, while being effective in recognizing and neutralizing the homologous venom, was far less able to recognize the venoms of *L. laeta* and *L. intermedia*. Its neutralizing capacity was almost nil, compared with the polyclonal antibodies generated against the same component of *L. gaucho* which adequately recognized and neutralized the venom of *L. intermedia*, and partially (60%) recognized that of *L. laeta*, suggesting the presence of different epitopes in the dermonecrotic components of these species, as well as differences in the composition and toxicity of these venoms (Guilherme et al., 2001). Moreover there is evidence of a marked cross-reactivity between the venoms of *L. reclusa* and *L. deserta* when the venom of either of the two species is used to generate antibodies (Goomez et al., 2001).

In general terms, there are two approaches for the treatment/prevention of poisoning by poisonous animals such as the violin spider: passive immunization (by means of serotherapic and fab-therapic agents) and active immunization (through vaccines); the former is a therapeutic measure, while the latter is rather a preventative measure.

Both venoms and isolated toxins have been used to generate vaccines. However, exposure to most venoms does not result in protective immunity. Furthermore, all attempts to create protective immunity against venoms, such as vaccines, have failed (Russell, 1971). In contrast, success has been obtained creating this type of immunity against individual toxins, including vaccines against diphtheria (Audibert et al., 1982), tetanus (Alouf, 1985), the toxoid of α-Latrotoxin (Alagón et al., 1998) and sphingomyelinase D of *L. laeta* (Araujo et al., 2003).

Passive Immunization

Aside from the palliative of some the palliative treatment of some of the specific symptom, the only treatment available for poisoning is passive immunization.

In the case of passive immunization, the antibodies or their fragments that will bind to the venom (antigen) are exogenous; i.e., they are produced in a first animal. The serum or antivenom from the first animal is then administered to the individual already affected by poisoning (host) to provide him with an immediate and active source of specific and reactive antibodies. The administered antibodies or their fragments will work then, in some sense, as if they were endogenous antibodies, binding the toxins of the venom and neutralizing their toxicity.

Depending on their final use, commercial generation of antivenoms can be undertaken, in various mammals such as mice, rabbits, goats, cows and horses, the horse being the animal of choice of moss laboratories since it is sturdy and tolerates the immunization process and especially because it produces high outputs (up to 16 L per bleeding).

However, there are some technical disadvantages to using horses for the production of antivenoms, among them, the need for large amounts of venom (immunogen or antigen) for performing immunization, forcing the laboratories to have large arachnariums or to contract out the work of gathering large collections of specimens in order to have sufficient quantities of venom available. For example, it is estimated that the production, evaluation and quality control of a lot of antivenom in horses requires highly standardized venom from five thousand spiders, which limits its commercial feasibility. Therefore, having recombinant immunogens capable of triggering an immune response comparable to that triggered by the administered venoms may be a significant alternative for the production of antivenoms, since stable and consistent immunogens would be produced in sufficient quantities at significantly lower costs and with fewer risks than those incurred by keeping arachanariums or the impact of massive collections on ecosystems.

In particular, there are two reports about the use of recombinant proteins as immunogens for the generation of antibodies against spider venoms in mammals, namely, the toxoid of α-Latrotoxin (Alagón et al., 1998) and a fusion protein that comprises the sequence of sphingomyelinase D of *Loxosceles intermedia* (Araujo et al., 2003).

In Mexico and Latin America, one of the main producers of antivenoms against the venoms of snakes and spiders (scorpions and black widow spiders) is the Instituto Bioclón, S. A. de C. V., which produces antibodies in horses and later purifies and hydrolyzes them in such a way that their antivenoms are in fact $F(ab')_2$ fragments of the antibodies, i.e., they are fabotherapics. Specifically, they produce antivenom against, the venom of the black widow spider, Aracmyn®.

Due to the variety of common and serious side effects of non-purified antivenoms, the physician must be extremely careful to avoid giving excessive amounts of equine products. A generally accepted theory is that the high incidence of side effects from the current horse antivenoms is caused by the excess of irrelevant protein they contain (irrelevant in the sense of not having a specific activity against the venom). According to this theory, the removal of that irrelevant protein could reduce the exogenous protein charge applied to the body and as a consequence, reduce the incidence of adverse immune responses.

Some researchers in the state-of-the-technique have considered the possibility of purification by immunoaffinity. Most of those studies have only tested antibodies against a single toxin; for example, Yang (1977) proved the purification by immunoaffinity of antibodies against a snake venom toxin. This researcher used cobratoxin, a neurotoxic protein isolated from the venom of the Taiwan cobra (*Naja naja atra*), bound to Sepharose, as an antigenic matrix and used formic acid to elute the toxin-specific antibodies. The antibodies thus purified were reported to have greater ability to neutralize the toxin than the non-purified serum.

Other researchers have been following similar purification schemes, such as Kukongviriyapan et al. (1982), who used the toxin 3 of *Naja naja siamensis* bound to several materials to form antigenic matrixes, obtaining a separation of horse-specific antibodies; Ayeb and Delori (1984), who also followed Yang's scheme to purify antibodies against scorpion-specific toxins; and Lomonte et al. (1985), who purified antibodies against the myotoxin of *B. asper* coupled to Sepharose.

Thus again, having recombinant sphingomyelinases that can specifically bind, preferably bound to an inert matrix, only those antibodies or their fragments that have a high specificity towards the necrotoxic component of the violin spider venom, may be of great help for removing the irrelevant protein for the treatment of poisoning, significantly reducing the risk of adverse immune reactions.

After an incident with *Loxosceles*, it is not uncommon for the treating physician, or even the affected patients or his/her parents in the case of children to, wrongly assume that it is the bite of an insect or of another type of spider, therefore applying insufficient or wrong treatment to the patient. By the time the unequivocal symptoms of loxoscelism start to appear, the necrosis of the tissue surrounding the wound may be quite advanced and can only be corrected using a skin graft. In this sense, it would be convenient to have an easily readable diagnostic system that allows the treating physician to determine during the first hours after the incident whether it is indeed a violin spider bite and to immediately start an effective treatment that prevents the development of necrosis.

BRIEF DESCRIPTION OF THE FIGURES

FIG. 4. Alignment of sequences of the 5 proteins with SMD activities, which comprised the recombinant proteins of this invention, with others reported in the literature is shown.

Figure 1:
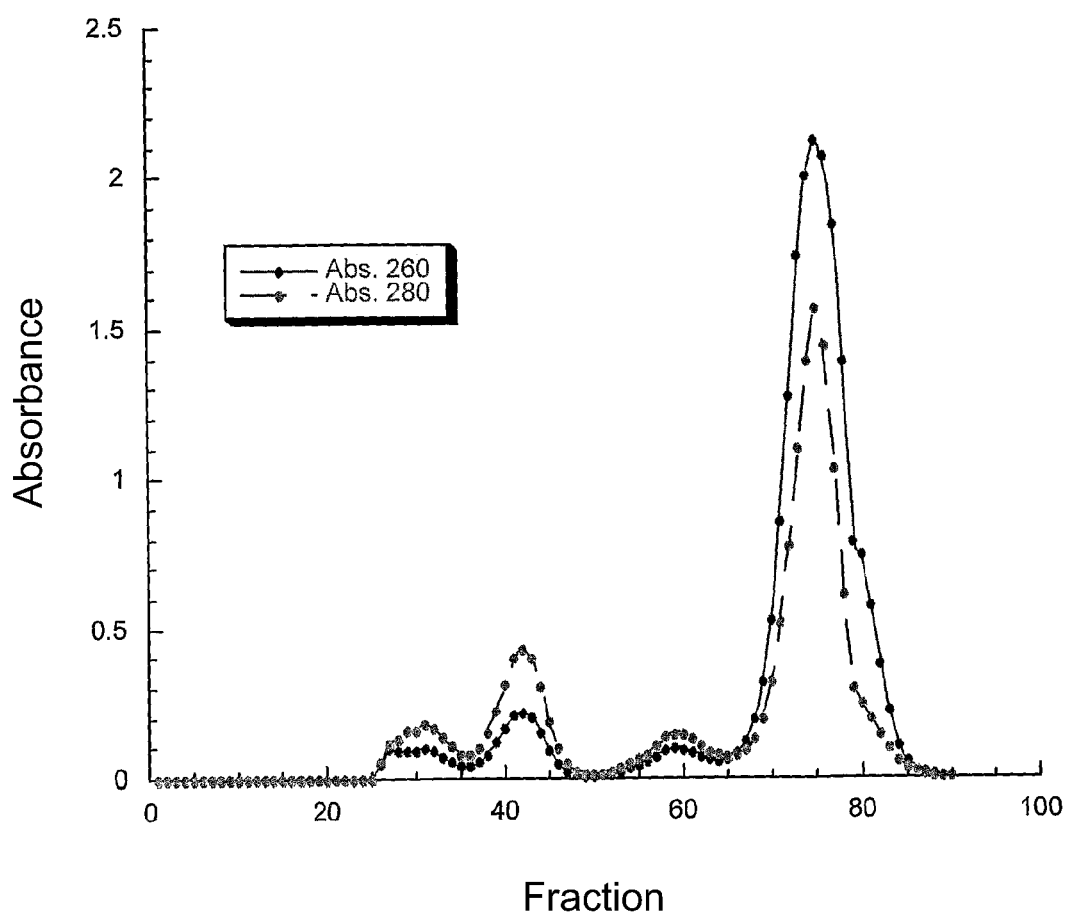
FIG. 1. Chromatogram of gel filtration of molecular exclusion (Sephadex G-75) of gland extract of *L. boneti*. The roman numerals correspond to the different fractions obtained. The red line corresponds to absorbance at 260 nm and the blue one at 280 nm.

| Access number in the Gene Bank: | | species |
|---|---|---|
| *Lb1. | AY559844 | *L. boneti* |
| *Lr1. | AY559846 | *L. reclusa* |
| *Lr2. | AY559847 | *L. reclusa* |
| *Ll1. | — | *L. laeta* |
| *Ll2. | — | *L. laeta* |
| La. | AAP44735 | *L. arizonica* |
| Li. | AAQ16123 | *L. laeta* |
| Ll.H17. | AAM21154 | *L. laeta* |
| LlH13. | AAN121155 | *L. laeta* |

*This patent

FIG. 5. The percentages of amino acid identity among the sphingomyelinases D of several species of *Loxosceles* are shown.

| Access number in the Gene Bank: | | species |
|---|---|---|
| *Lb1. | AY559844 | *L. boneti* |
| *Lr1. | AY559846 | *L. reclusa* |
| *Lr2. | AY559847 | *L. reclusa* |
| *Ll1. | — | *L. laeta* |
| *Ll2. | — | *L. laeta* |
| La. | AAP44735 | *L. arizonica* |
| Li. | AAQ16123 | *L. laeta* |
| Ll.H17. | AAM21154 | *L. laeta* |
| LlH13. | AAN121155 | *L. laeta* |

*This patent

DETAILED DESCRIPTION

Definitions.

The term "antibody" is used to refer to polyclonal antibodies and their fragments.

The term "fragment", when referring to antibodies, comprises a portion of the whole antibody, generally the fragment of antigen binding, e.g. fragments Fab, Fab', F(ab')$_2$, and Fv.

The terms "neutralize" or "neutralizing" or "neutralizing antibodies" refer to the ability of the antibodies of this invention to bind to the sphingomyelinase D of spiders of the *Loxosceles* genus, whether isolated or as part of the whole venom of those spiders, and to cancel its toxic effect and that of the said venom.

The term "treatment" refers to therapeutic treatment. Those that need treatment include those individuals bitten by one or more spiders of the *Loxosceles* genus.

The term "toxoid" refers to a mutant version of the recombinant proteins (recombinant SMD) object of this invention that lack enzymatic and dermonecrotic activity, but that retain the property of generating antibodies that neutralize the venom of the *Loxosceles* spider when used to immunize vertebrates, and in particular, mammals.

The term "pharmaceutically acceptable carrier" refers to a solid or liquid excipient, diluent or substance that can be used safely for systemic or topic administration. Depending on the particular route of administration, a variety of pharmaceutically acceptable carriers well-known in the state of the art includes solid or liquid excipients, diluents, hydrotopes, surface active agents, and encapsulating substances. The amount of carrier used in conjunction with the antibodies or their F(ab')$_2$ fragments provides a practical manageable amount of material by unitary doses of the composition.

Acceptable carriers for systemic administration that can be incorporated into the composition of this invention include sugar, starches, cellulose, vegetable oils, buffers, polyoles, and alginic acid. The specific pharmaceutically acceptable carriers are described in the following documents, which are hereto incorporated by reference: U.S. Pat. No. 4,401,663 Buckwalter et al., issued Aug. 30, 1983; European patent application No. 089710, LaHann et al., published Sep. 28, 1983; and European patent application No. 0068592, Buckwalter et al., published Jan. 5, 1983. The preferred carriers for parenteral administration include propylene glycol, pyrrolidol, ethyl oleate, aqueous ethanol and combinations thereof.

Representative carriers include acacia, agar, alginates, hydroxyalkylcellulose, hydroxypropyl-methyl-cellulose, carboxymethylcellulose, carrageenin, powdered cellulose, guar gum, cholesterol gelatin, agar gum, gum Arabic, gum karaya, ghatti gum, carob gum, octoxinot 9, allylic alcohol, pectin, polyacrylic acid and its homologues, polyethyleneglycol, polyvinylic alcohol, polyacrylamide, sodium lauryl sulphate, polyethylene oxide, polyvinylpirrolidone, glycol monostearate, propyleneglycol monostearate, xanthan gum, tragacantum, sorbitan esters, estearylic alcohol, starch and its modifications. The appropriate ranges vary from around 0.5% to around 1%.

As can be seen from the aforementioned, unlike the problem of poisoning by the black widow spider (*Latrodectus mactans*), for which there are already some treatments using antivenoms, (F(ab')$_2$ fragments of horse polyclonal antibodies), for loxoscelism, there is still no commercial treatment. The generation of antivenoms by immunization with the venom of the spider could be an alternative; however, it has the disadvantage of requiring a large number of spiders (about 5,000 per batch) to extract enough amounts of the venom. Also, its use implies that the serum produced by the animal contains large amounts of antibodies against the varied proteins of the venom, most of them have either minimal or no effect on the poisoning process in mammals, and therefore the antibodies against those proteins have little value for treating the poisoning and instead, they contribute large amounts of proteins that are exogenous to the organism being treated, potentially causing severe side effects. In general, some approaches that have been followed to reduce that amount of protein have been separating the immunoglobulin fraction of the serum, eliminating other serum proteins (such as albumin) by precipitation with ammonium or sodium sulphate, with the corresponding decrease of the neutralizing activity, and hydrolyzing that fraction with tripsin or pepsin to release the F(ab) fragments or $F(ab)_2$, that preserve the neutralizing activity. However, the antibody fraction or their fragments continue to have a high proportion of irrelevant protein (because they are antibody fragments against all the components of the whole venom and against multiple undefined antigens).

This problem could be resolved through immunoaffinity purification if there were an immunogen matrix that allowed for the specific separation of the source from the immunoglobulins or from the fragments produced by their hydrolysis, those specific antibodies or fragments, responsible for neutralizing the toxic effect of the whole venom.

On the other hand, as mentioned before, there is a need for a reliable diagnostic system that allows the attending physician to determine quickly and easily whether he is dealing with a *Loxosceles* bite, and then to be able to immediately administer an appropriate treatment that prevents the necrosis of the tissue surrounding the area of the bite.

In order to solve these problems, the inventors of this invention have undertaken to characterize the venom of *L. boneti*, isolating and purifying its dermonecrotic component and to isolate and characterize its codifying DNA, as well as the codifying DNA of the dermonecrotic component of *L. reclusa* and *L. laeta* (Peruvian variety), to clone the codifying sequences into appropriate expression vectors, to express the active recombinant proteins, and test them regarding their ability to generate an effective immune response for the neutralization of the neurotoxin and the whole homologue venom, as well as in cross-reaction tests of the venom of these species of *Loxosceles*.

The active recombinant proteins of *L. boneti* (SMDrLb), *L. reclusa* (SMDrLr), and *L. laeta* (Peruvian variety) (SMDrLl) may be used as immunogens to generate antivenoms in vertebrates; bound to solid or semisolid substrates to generate antigenic matrixes useful for immunopurification of antivenoms; and in the design and construction of diagnostic systems to determine if a patient suffers from loxoscelism.

As shown in Example 1, the inventors of this invention separated the whole venom of *L. boneti* into fractions, finding that only fraction II shows dermonecrotic activity. They were able to separate 3 isoforms of the dermonecrotic component. They found that only isoforms I and II are active, the former being the more active one, and they obtained an amino acidic sequence of the amino terminus of the three isoforms, which were used to design the specific oligos for obtaining the clones of the necrotoxic components from the RNAm extracted from the venom glands of the spiders (see Example 3), clone 30-8 being the one selected for its expression. For this purpose, clone 30-8 was subcloned in the pTrcHIS-TOPO plasmid, obtaining pTrcHIS-TOPO 30-8 plasmid (see details in Example 4) and expressed in *E. coli* XL1 Blue, obtaining its expression in the form of inclusion bodies that were solubilized and refolded. The solubilized and refolded recombinant protein lacked sphingomyelinase D (SMD) and dermonecrotic activity and the antibodies generated in rabbits against it; although capable of recognizing the protein through Western Blot, they were not able to neutralize the whole venom of the *L. boneti* spider.

After an analysis, the following factors were taken into consideration in an effort to express the recombinant protein in a soluble and active form: (i) the sequence of the fragment used lacked the first 4 codons, hence the amino acidic sequence of the recombinant protein lacked the first 4 amino acids of the extreme amino terminus; (ii) just before the BamH I cut site, vector pTrcHIS-TOPO has the 36 AA sequence, including the initial methyonine and a tail of 6 histidines useful for the recovery of the protein which, plus the 2 codons occupied by the BamH I site, add a total of 38 amino acids to the recombinant protein, which amino acids could be responsible for its poor plication, and (iii) it is known (see pET System Manual) that certain strains of *E. coli* may favor the adequate plication of some the recombinant proteins they express. Additionally, the successful expression of the recombinant protein comprising the amino acidic sequence of one of the isoforms of sphingomyelinase D of *L. laeta* in *E. coli* BL21 had been reported (Fernandes Pedroza et al., 2002).

Therefore it was decided to complete the codifying sequence (the 4 missing amino acids) as shown in Example 5; changing to the pQE-30 expression vector that only adds 12 amino acids to the recombinant protein at its extreme amino terminus, and expressing it in the BL21 strain of *E. coli* (see Example 6). Again, an expression in the form of inclusion bodies was obtained which, although considerable, had negligible enzymatic activity.

It is known that if the expression is too high, all the protein accumulates in the form of inclusion bodies, thus it may be advisable to try to reduce the protein expression. Whit this finality, a controlled expression of the protein was performed, as detailed in Example 7, this time managing to express the protein both as inclusion bodies and soluble. Once the protein was purified was proved to have the same specific activity as have the native isoform I, and with an LD50 of 2.55 μg per mouse.

The soluble recombinant sphingomyelinase D of *L. boneti* (SMDrLb) thus produced was used to inoculate rabbits (see Example 8) obtaining titles of up to 29,300. The resulting antibodies were neutralizing for both the active recombinant protein (ESD50=154.6 μL/mouse for 78 μg of the antigen), and the native venom of *L. boneti* (ED50=149.64 μL/mouse with 3 LD50 of the native venom).

Based on the experiment followed to obtain the sphingomyelinase D (the dermonecrotic component) of *L. boneti*, we proceeded to obtain the sphingomyelinase D of *L. reclusa* and *L. laeta* (Peruvian variety). In the first case, the amino acidic sequence of the first 34 amino acids of the amino terminus of the sphingomyelinase D of *L. recluse* is known from the literature (Barbaro, K. C. et al., 1996), and upon exact coincidence of the first 5 amino acids with those corresponding to *L. boneti*, we decided to use the same oligos to obtain the cDNA of the dermonecrotic component from the RNAm extracted from the glands of the spider (see Example 9). In this case, the cDNAs of two active isoforms of the SMD of L. reclusa were obtained, SMDrLr1 and SMDrLr2 (with 90% of similarity between them) with an activity of 27.2 U/mg for SMDrLr1 and 11.47 U/mg for SMDrLr2. As was the case with L. boneti, the inventors subcloned the clones in the pQE-30 plasmid, and they were expressed in a controlled way in the BL21 strain of E. coli (see Example 10). To exemplify their use as immunogens for generating neutralizing antibodies from the venom of L. reclusa spiders, one of the soluble and active recombinant sphingomyelinases D of L. reclusa thus produced, SMDrLr1, was used to inoculate rabbits (see Example 11), resulting in titres of up to 3300. The resulting antibodies were neutralizing for both the active recombinant protein (ED50=165 µL/mouse for 12 µg of the recombinant protein), and the native venom of the L. recluse spider (ED50=175 µL/mouse with 12 µg of the venom).

In the second case, the complete amino acidic sequence of some of the active isoforms of sphingomyelinase D) of L. laeta (Brazilian variety) is known from the literature (Fernandes Pedrosa et al., 2002). Based on them, the L15'Bam HI and L13'Sal I oligos were designed to obtain the cDNA of the dermonecrotic component from the RNAm extracted from the glands of the spider (see Example 12). In this case, the inventors succeeded in isolating the cDNA of 2 distinct and active isoforms: the former, SMDrLl1, with an activity of 58.43 U/mg, and the latter, SMDrLl2, with an activity of 252 U/mg. As was the case with L. boneti and L. reclusa, the inventors subcloned the clones in the pQE-30 plasmid, and they were expressed in a controlled way in the BL21 strain of E. coli (see Example 13). When the codifying DNA fragments were sequenced, one of the codified proteins, SMDrLl1, showed a primary sequence slightly different (99% of similarity) from that reported by Fernandes Pedrosa et al. for isoform H17 (which is the isoform he reports as active), while SMDrLl2, which in this invention proves to have almost 3 times the activity of SMDrLl1, showed a sequence 94% identical to isoform H13 that is reported by Fernandes Pedrosa et al. as inactive. To exemplify their use as immunogens for generating neutralizing antibodies from the venom of the L. reclusa spider, one of the soluble and active recombinant sphingomyelinase D of L. laeta (Peruvian variety) thus produced, SMDrLl1, was used to inoculate rabbits (see Example 14), obtaining neutralizing antibodies both from the active recombinant protein (DE50=200 µL per mouse for 12 µg of protein) and from the native venom of the L. laeta spider (Peruvian variety) (DE50=225 µL per mouse of venom).

The recombinant proteins of this invention, SMDrLb, SMDrLr1, SMDrLr2, SMDrLl1, and SMDrLl2, were expressed using the pQE30 plasmid, which adds a sequence of 12 amino acids—MRGSHHHHHHGS (SEQ. ID. NO: 25) that include a tail of 6 histidines—to the amino region (amino versions) of the protein. However, they can be expressed in other expression systems that introduce other amino acid sequences to either the amino terminus or the carboxyl of the proteins. One example is pQE60 plasmid (INVITROGEN), which includes only the Methionine, Glycin and Serine amino acids in the amino region while in the carboxyl terminus it includes an 8-amino acid sequence RSHHHHHH (SEQ. ID. NO: 26). In Example 16, the Lb1, Lr1, Lr2, and Ll2 clones were subclonated in the pQE60 plasmid and were expressed in a controlled way to obtain the carboxyl versions of the proteins (with the Histidine tail in that terminus). The recombinant proteins obtained, which like the corresponding amino versions comprise the sequences SEQ.ID.NO:11, SEQ.ID.NO:13, SEQ.ID.NO:15, and SEQ.ID.NO:21, were active.

One scope of this invention, then, refers to the SMDrLb, SMDrLr1, SMDrLr2, SMDrLr2, SMDrLl1, and SMDrLl2 recombinant proteins, either their amino versions (with the Histidine tail at the amino terminus) or their carboxyl versions (with the Histidine tail at the carboxyl terminus), that comprise the native sphingomyelinase D sequences of L. boneti, L. reclusa and L. laeta spiders. SEQ. ID. No: 11, SEQ. ID. No: 13, SEQ. ID. No: 15, SEQ. ID. No: 19, and SEQ. ID. No: 21 respectively or variants or mutants of those sequences, and that show sphingomyelinase D activity.

Another scope of this invention refersts to the DNA fragments that comprise the codifying sequences of the recombinant proteins SMDrLb, SMDrLr1, SMDrLr2, SMDrLl1, and SMDrLl2, with the SEQ. ID. No: 10, SEQ. ID. No: 12, SEQ. ID. No: 14, SEQ. ID. No: 18, and SEQ. ID. No: 20, respectively; its obtaining is detailed in Examples 5, 9, and 12.

It is known that the genetic code is degenerated, i.e., for one amino acid there is usually more than one codifying codon; generally, the difference among these codons is at the third base position. It is obvious to an expert in the state of the technique that it is possible to perform substitutions of some bases in any of the codifying nucleotide sequences of the recombinant proteins of this invention (SMDrLb, SMDrLr1, SMDrLr2, SMDrLl1 and SMDrLl2), that codify exactly the same amino acidic sequences as those present in SEQ ID NO: 11, SEQ ID NO: 13, SEQ ID NO: 15, SEQ ID NO: 19, and SEQ ID NO: 21, generating "silent mutations" of those sequences. This can be especially useful when one wants to express the recombinant proteins of this invention in various recombinant hosts, since it is known that different kinds of hosts have a "preference" of use towards certain codons for particular amino acids. Such "silent mutations" fall within the scope of this invention since the products of their expression are once again the same recombinant proteins SMDrLb, SMDrLr1, SMDrLr2, SMDrLl1 and SMDrLl2 of this invention.

Moreover, it is also obvious for an expert in the state of the technique that it is possible to substitute some amino acids outside the active site of the protein for others of the amino acidic sequences with similar characteristics; e.g., one polar amino acid for another polar amino acid, an aromatic one for another aromatic one, a charged one for another, etc. It is not expected that such mutations produce significant changes in the activity of recombinant proteins, hence those point- or site-specific mutations for the codifying DNA fragments of the recombinant proteins of this invention that produce functionally equivalent proteins (i.e., those that have sphingomyelinase D activity and that cause dermonecrosis in a mammal inoculated with them) are included within the scope of this invention.

An additional scope of this invention refersts to mutants of the recombinant proteins object of this invention and their codifying DNAs, which constitute toxoids of those proteins, i.e., they lack enzymatic activity as sphingomyelinase D and the dermonecrotic effect, but they retain the property of being expressed in a soluble form with the methods described above and of generating antibodies, that neutralize the venom of Loxosceles spiders by inoculating vertebrates—especially mammals.

Particularly based on the description of the active center of one of the isoforms of sphingomyelinase D of L. laeta (Murakami et al., 2005), where it is made evident that the binding to the substrate and the transition state of the enzyme are stabilized by the $Mg^{2+}$ ion, which forms a coordination binding with the Glu32, Asp34, and Asp91 amino acids and molecules of the solvent.} The amino acids His12 and His47 play a key role in the acid-base catalytic mechanism proposed by the authors (all of the amino acids are counted from the extreme amino terminus of the mature protein). Therefore, those 5 amino acids prove to be especially attractive blanks for performing a directed mutagenesis method to try to obtain mutants that are toxoids of the sphingomyelinases D of *Loxosceles* spiders. In *L. boneti* and *L. reclusa*, the equivalent of these amino acids are Glu31, Asp33 and Asp91, and the His11 and His47 histidines. Special attention was given to the idea that effecting the mutations on Glu32 (or Glu31 for *L. boneti* or *L. reclusa*) would be highly attractive for performing the substitution of an amino acid that breaks the coordination bond with the $Mg^{2+}$ ion, and on His12 (or His11 for *L. boneti* or *L. reclusa*) it would be highly attractive for performing the substitution of an amino acid that, without interfering with the dimerization of sphingomyelinase D, makes it lose its enzymatic activity.

To prove this, by way of illustration but without limitation, as shown in Example 18, a toxoid for the recombinant protein SMDrLb was built, substituting Histidine 11 with Lysine and generating the SEQ.ID.No: 27 that codifies for the amino acidic sequence SEQ.ID.No:28. Simultaneously, a toxoid for the same SMDrLb recombinant protein with the Glu31 substituted by Lysine was built, generating the SEQ.ID.No:29 that codifies for the amino acidic sequence SEQ.ID.No:30. These mutations cause the proteins (SMDrLb(H11K) and SMDrLb(E31K), respectively) expressed by the above-mentioned methods to lack enzymatic activity as sphingomyelinase D and the dermonecrotic effect, but to retain the property of being expressed in a soluble form with the methods described above and of generating, by inoculation of vertebrates—particularly mammals—, antibodies that neutralize the venom of the *Loxosceles* spider (at least that of *L. boneti*).

Another scope of this invention refers to the expression vectors in which are cloned the DNA fragments that comprise any of the following sequences: SEQ. ID. NO: 10, SEQ. ID. NO: 12, SEQ. ID. NO: 14, SEQ. ID. NO: 18, SEQ. ID. NO: 20, SEQ. ID. NO: 27, and SEQ. ID. NO: 29. There is a great variety of expression vectors so when selecting them, it is important to consider that the number of amino acids added to the recombinant proteins not to be so high as to drastically reduce the solubility and/or activity of the expression product. Some examples of expression vectors are pQ30 and pQ60 by Qiagen. Obviously another element to consider during selection is the bacterial strain to be used.

Another scope of this invention refers to the recombinant bacterial strain to be used in the expression of the recombinant proteins object of this invention. *Escherichia coli* is the best known bacterial species and is widely used for the expression of recombinant proteins, hence the recombinant bacterial strain of this invention is preferably from this species. As has been previously mentioned, some strains favor the plication of the recombinant proteins that they express. An example of this kind of strain is *Escherichia coli* BL21. Thus the recombinant bacterial strain of this invention is preferably *E. coli* BL21.

Another scope of this invention refers to the recombinant methods to produce the SMDrLb, SMDrLr1, SMDrLr2, SMDrLl1, SMDrLl2 proteins or their toxoids through the use of DNA fragments with the sequences SEQ. ID. No: 10, SEQ. ID. No: 12, SEQ. ID. No: 14, SEQ. ID. No: 18, SEQ. ID.No: 20, SEQ. ID. NO: SEQ. ID. NO: 27, and SEQ. ID. NO: 29, respectively. This is illustrated in Examples 7, 10, and 13.

Thus a general method for the production of the recombinant proteins object of this invention is comprised of the following steps:

(a) incubating in an adequate medium and in adequate culture conditions a transformed recombinant bacterial strain with an expression vector that comprises a DNA fragment selected from the group that consists of DNA fragments with the SEQ. ID. NO: 10, SEQ. ID. NO: 12, SEQ. ID. NO: 14, SEQ. ID. NO: 18, SEQ. ID. NO: 20, SEQ. ID. NO: 27, and SEQ. ID. NO: 29 sequences.

(b) optionally, separating the cellular mass from the medium;

(c) breaking the cells to release the protein, and (d) optionally, separating and purifying the recombinant protein.

The selection of the vector-host expression system may be varied. In this invention, by way of illustration but without limitation, the BL21 strain of *E. coli* was selected to be used in the production methods of the recombinant proteins of this invention; a controlled expression of them was made by means of an IPTG 0.1 mM induction, so that preferably, when an adequate cellular mass is reached using the method for producing the recombinant proteins object of this invention, the expression is induced with the concentration of IPTG of 0.1 mM at a temperature of between 20 and 25° C. for at least 12 to 20 hours.

Another scope of this invention refers to the use of the recombinant proteins SMDrLb, SMDrLr1, SMDrLr2, SMDrLl1, SMDrLl2, SMDrLb(H11K) and SMDrLb(E31K) as immunogens to generate neutralizing antibodies of the whole venom of *Loxosceles* genus spiders in vertebrates with the purpose of industrially producing antivenoms against the venom of those spiders. This is clearly illustrated in Examples 8, 11, and 14 with rabbits, and in Example 17 with horses; although the production of antibodies in fowl, such as hens, is also known. For that purpose an immunogenic composition that includes at least one of the recombinant proteins object of this invention is used. Typically, an immunogenic composition of this type may additionally include a pH buffer system and an adjuvant, such as the complete or incomplete Freund's adjuvant. According to this invention, a method for producing neutralizing antibodies for the venom of the spiders of the *Loxosceles* genus involves inoculating a vertebrate with an effective amount sufficient to generate antibodies of an immunogenic composition similar to the one described above, that includes at least one of the recombinant proteins of this invention. The vertebrate, preferably a mammal, may be, among others, a rabbit, a sheep, a goat or if possible, a horse, as illustrated in Example 17. Preferably, that method includes recovering the antibodies from the animal, typically from blood serum or plasma. Preferably, those antibodies are neutralizers of the in vivo toxic effect of the whole venom of the *Loxosceles* spider, preferably from species selected from the group that comprises *L. boneti, L. reclusa* and *L. laeta*.

An additional scope of this invention refers to the compositions that comprise the antibodies, or their antigen-binding fragments, that neutralize the in viva effect of the venom of the *Loxosceles* spider, produced by the method described above. Those compositions comprise antibodies generated against at least one of the recombinant proteins object of this invention. Preferably, the spider belongs to a species selected from the group consisting of *L. boneti, L. reclusa* or *L. laeta*.

Since the antibodies generated against the recombinant proteins object of this invention, whether in an isolated form or as a mixture of immunogens, have proven to be neutralizers of the venom of the *Loxosceles* spider, they may be used as part of a pharmaceutical composition to treat patients who have been bitten by *Loxosceles* spiders, especially *L. boneti, L. reclusa* and *L. laeta*. Optionally, the pharmaceutical composition may include pharmaceutically acceptable carriers like the ones described above.

According to this, another scope of this invention refers to pharmaceutical compositions that comprise the neutralizing antibodies (or their fragments) produced by means of the methods described above, using one or more of the recombinant proteins object of this invention as immunogens, where said composition neutralizes the toxic effect of the venom of the *Loxosceles* spider and is useful for the treatment of individuals who have been bitten by that *Loxosceles* spider.

In another scope, this invention refers to a method for treating individuals who need such treatment, particularly individuals that have been bitten by *Loxosceles* spiders, particularly *L. boneti. L. reclusa* and *L. laeta*, where that method consists of the administration of a pharmaceutically effective amount of the pharmaceutical composition described above. The pharmaceutical composition may be locally or systemically administered by intravenous, subcutaneous, intramuscular, vaginal, intraperitoneal, nasal, or oral routes to protect the individuals from the toxic effect of *Loxosceles* spider venom.

The recombinant proteins object of this invention (SMDrLb, SMDrLr1, SMDrLr2, SMDrLl1, SMDrLl2, SMDrLb (H11K), and SMDrLb(E31K)), may also be used to generate an antigenic matrix when bound, either covalently or by hydrophobic or hydrophilic interactions, to a substrate such as polyacrylamide, polyvinyl, activated aldehyde-agarose (U.S. Pat. Nos. 5,904,922 and 5,443,976), sepharose, carboxymethyl cellulose or some other, in such a way that that matrix is capable of binding specifically to either antibodies (generated against the whole venom of *Loxosceles* spiders or against those same venoms enriched with some of the recombinant proteins object of this invention, or against a mixture of those recombinant proteins object of this invention) or against the F(ab) or F(ab')2 fragments obtained from the hydrolysis of such antibodies, being useful for purifying those antibodies or F(ab) or F(ab')2 fragments by immunoaffinity, so the use of the recombinant proteins object of this invention in the antigenic matrix and said antigenic matrix are included in the scope of this invention. This immunopurification of the antibodies or their fragments during the antivenom manufacturing process will help to decrease the proportion of the irrelevant exogenous protein administered to a patient bitten by a *Loxosceles* spider. Therefore, another aspect of this invention is a composition that includes at least one of the recombinant proteins object of this invention, bound to a substrate, characterized by the fact that composition is capable of binding specifically to the antibodies generated against the venom of the *Loxosceles* genus spiders or against that venom enriched with at least one of the recombinant proteins object of this invention.

Another scope of this invention refers to the use of the recombinant proteins object of this invention (SMDrLb, SMDrLr1, SMDrLr2, SMDrLl1, SMDrLl2, SMDrLb(H11K) and SMDrLb(E31K)) in diagnosis. Through the use of any of the recombinant proteins of this invention, it is possible to generate specific monoclonal antibodies against an epitope present only in that recombinant protein or in the corresponding native toxin of the venom of the homologous species of *Loxosceles* spiders, but absent in the toxin of the venom of the other *Loxosceles* species. These recombinant proteins may be used as part of an antigenic matrix in which they are bound covalently or by hydrophobic or hydrophilic interactions to a substrate, and that matrix may be used as part of a diagnostic device. By testing a sample of an individual supposedly bitten by a *Loxosceles* spider, said device will be able to be used to detect the presence, in a sample of antibodies generated, by the body of the individual, specifically against the homologous native toxin of the venom of a specific *Loxosceles* spider, determining if the spider that bit the individual belonged to that species of *Loxosceles*. This can be done with each of the recombinant proteins object of this invention, which would help to determine which of the homologous species (*L. boneti, L. reclusa* or *L. laeta*, Peruvian variety) the spider that caused the bite belongs to, providing the attending physician with a tool for directing the treatment specifically. A method to diagnose whether the animal that bit the individual belongs to a particular species of *Loxosceles* spider will include putting the above-mentioned device in contact with a sample of the individual bitten. If they are present, the antibodies generated specifically against the natural toxin of the venom of the spider that bit the individual will recognize and bind to one of the recombinant proteins of the device. An optional detection system may be used to reveal the presence of the antibodies of the sample bound to the recombinant protein of the device. This detection system may be based on immune-enzymatic, immune-fluorescence or immune-chromatographic methods.

Materials and Methods

1. Spiders

The specimens of *L. boneti* were gathered by people trained to recognize the *Loxosceles* genus in the communities of La Capilla and Corral de Toros, municipality of Iguala, which are located in the central region of the State of Guerrero, Mexico, according to the distribution determined by Hoffman (1976) and Gerstch (1983). To confirm this, 10 female and 10 male spiders were sent to the Museum of Natural History of New York to Dr. Norman Platnich, who identified them as such. The specimens of *L. reclusa* were collected in Stillwater, Okla. by the inventors of this invention, while the specimens of *L. laeta* (Peruvian variety) were collected in Lima, Peru.

2. Obtaining the Venom

The glands of the spiders were mechanically extracted, by pulling the chelicerae to uproot them. They were placed in an ammonium acetate buffer 20 mM pH 4.7 and were macerated with a Teflon homogenizer (50 venom apparatuses per mL); they were centrifuged for two minutes at 14,000 rpm to remove the undesired solid residues and cellular remains; they were stored at −70° C. until their use.

Limited amounts of pure venom (different from the gland extract described) were also obtained. For that purpose, we took advantage of the fact that when manipulated, some spiders secrete small amounts of venom; those were collected in microcapillary tubes.

3. Biochemical Tests (a) Molecular Exclusion Gel Chromatography

A 170 cm long and 1.4 cm in diameter column was used. The resin selected to pack the column was Sephadex G-75 (SIGMA CHEMICAL CO.) because its exclusion limit is 70 kDa. The run buffer was ammonium acetate 20 mM, pH 4.7. The flow speed in the experiment was of 48 mL $h^{-1}$ $cm^{-2}$.

72.56 mg of venom (3.5 mL) were applied, measured by absorbance at 280 nm. Samples were collected every six minutes with an approximate volume of 4.5 mL; the spectrophotometer (Beckman DU650i) was read at two wavelengths: 260 nm and 280 nm.

(b) Polyacrylamide Gel Electrophoresis (SDS-Page).

The proteins were separated from the venoms in polyacrylamide gels at 12.5% in reducing conditions at constant current. The equipment used for this method was the Mini Protean III (BIO-RAD). Different concentrations were used for each sample subjected to electrophoresis.

For the reducing conditions, 2-mercaptoethanol was used at a final concentration of 25%. The prestained molecular weight markers (BioLabs, Inc.) were used as molecular weight standards. All the samples, including the molecular weight marker, were previously denaturalized in a water bath for 5 minutes. These were run at a constant current of 15 mA, until the dye penetrated the separating gel; subsequently, the current was increased to 25 mA. Once the gel run was finished, we proceeded to perform staining with Coomnassic bright blue for one hour, and it was decelerated with a solution of 10% of acetic acid and 25% of methanol overnight with constant agitation.

(c) Ion-Exchange Chromatography (FPLC)

The column used was of the Mono S HR 5/5 type (Pharmacia LKB Biotech), which is a strong cation exchanger based on hydrophilic resins. The flow used for the runs was 1 mL/min. The buffers used were the following:

Initial buffer: Buffer A—Ammonium acetate 20 mM, pH 4.7,

Buffer limit: Buffer B—Ammonium acetate 20 mM, pH 4.7+2 M sodium chloride.

Both buffers (filtrated through a 0.22 micron membrane) were run to calibrate the column according to the distributor's specifications:

Once the column was balanced, the sample was injected. The sample was previously centrifuged for two minutes at 14,000 rpm, to clarify it (remove residues and/or precipitates).

The sensitivity of the detector was 0.2 AU, the flow rate was 1 mL/min and the gradient was from 0 to 2 M sodium chloride.

4. Activity of Sphingomyelinase D.

The measurement of this enzymatic activity was done with the Amplex Red Sphingomyelinase Assay Kit (Molecular Probes) following the protocol suggested by the manufacturer, using serial dilutions (1:1) starting from 1 µg/ml.

5. Measurement of Titers by ELISA of the Sera and In Vitro Determination of Cross-Reactions The titration of antibodies from sera was performed by Enzyme-Linked Immuno Assays (ELISA). This assay was also used to observe possible cross-reactions.

The ELISA assay consisted of:

1. Sensitization of 96-well plates for ELISA (Maxi sorp, NUNC™ Brand products) with a an antigen solution at a concentration of 5 µg/mL, reconstituted in 100 mM carbonate/bicarbonate pH 9.5.

100 µL were dispensed in each well up to column 11, since track 12 served as negative control. The plate was incubated overnight at 4° C.

2. Once the incubation was completed, it was washed three limes with 200 µL of washing solution. This process had to be repeated each time we advanced to the next step along the complete technique.

3. Afterwards, the unspecific protein binding sites were blocked with 200 µL of blocking solution, for 2 hours at 37° C.

4. Step 2 is repeated,

5. Serial dilutions of the sera with an initial dilution of 1:30 in an ELISA reaction buffer (indicated in the corresponding addendum) were made. 100 µL of the ELISA reaction solution were added to each well, and 50 µL/well of the antiloxosceles serum dilution were mixed in column 1, to proceed to the 3× serial dilutions up to column 10 leaving columns 11 and 12 as controls. It was incubated for one hour at room temperature.

6. Repeat step 2.

7. Then the second anti-rabbit antibody conjugated with the peroxidase enzyme diluted to 1:1000 in an ELISA reaction solution was incubated, placing 100 µL/well. The incubation time was 1 hour at room temperature.

8. The reaction was revealed with 100 µL/well of ABTS substrate (Boehringer), incubating for 5 minutes at room temperature. After five minutes, the reaction was stopped with 25 µL of fluorhydric acid (Aldrich), and the plate was read in an ELISA plate reader (model BIO-RAD 550) at 405 nm.

To determine the titers of the readings obtained, the sigmoid curves were generated with the GraphPad Prism software (Version 2; GraphPad Software, Inc, San Diego, Calif.). The inflection point was calculated by adjusting the experimental data for each venom and each antivenom by nonlinear regression of the sigmoid curves.

6. Western Blot Tests

This is a technique used to identify which mixture of proteins or their fragments react to a determined antibody or antiserum. Western Blot tests were performed according to the Mathews and Holde protocol (1998).

Polyacrylamide gels 12.5% were prepared and run in the usual way to separate the proteic components of the venoms of *L. boneti* and *L. reclusa*. The amount of venom used for each assay was 30 µg per track. Once the gel run was completed, the transference to a nitrocellulose membrane (solid substrate) was performed during one hour at constant current (400 mA).

6. Western Blot Tests

This is a technique used to identify which proteins, or their fragments, within a mixture react to a particular antibody or antiserum. Western Blot tests were performed according to the Mathews and Holde protocol (1998).

12.5% polyacrylamide gels were prepared and run in the usual way to separate the proteic components of the venoms of *L. boneti* and *L. reclusa*. The amount of venom used for each assay was 30 µg per track. Once the gel run was completed, the transference to a nitrocellulose membrane (solid substrate) was performed for one hour at constant current (400 mA). For this purpose, a transference chamber under semi-humid conditions was used (OWL) Once the transference to the membrane was completed, it was blocked overnight with constant stirring at room temperature in a 5% solution of skimmed milk/TBST, to prevent the unspecific binding of the antibodies. After this time, the membranes were washed three times with TBST 1× (ten minutes each washing). Afterwards, It was incubated with the first antibody in 0.1% powdered skimmed milk (Carnation or Svelty/TBST) with constant stirring at room temperature for one hour (it was diluted according to the titre of the antibody). The dilutions used in this assay were 1:1000, 1:2500, and 1:5000.

Once the incubation was completed, we performed three ten-minute washes each one with TBST 1×. The second antibody was incubated for one hour at room temperature with constant stirring in 0.1% skimmed milk/TBST. An anti-rabbit coupled to alkaline phosphatase (ZYMED) was used as the second antibody.

After the incubation, it was washed three times with TBST for ten minutes; the TBST from the last wash was eliminated, and NTB-BCIP reaction buffer, which was left to react for five minutes, was added; the reaction was stopped with 5 mM EDTA.

7. Determination of the LD50

To determine the LD50 of SMDrLb and SMDrLr of the native venoms of *L. reclusa* and *L. boneti*, groups of 5 Balb/c mice weighing 18-20 g were used. Variable amounts of the toxin were applied intraperitoneally, ranging from 0.6 to 17.57 μg of toxin per animal, and an LD50 of 2.55 μg of SMDrLb and of 6 μg of SMDrLr were found per mouse. The SMDrLb used had a concentration of 331 μg/mL (BCA method) and a sphingomyelinase D activity of 104.77 U/mL; the SMDLr had a concentration of 53.6 μg/mL and a sphingomyelinase D activity of 103.38 U/mL. The calculations were made using the GraphPad Prism software (Version 2; GraphPad Software, Inc, San Diego, Calif.). The venoms used had a concentration of 3,300 μg/mL of protein (BCA) and a sphingomyelinase D activity of 7.5 U/mg for *L. boneti*, and 5,800 μg/mL (BCA) and 9.05 U/mg for the venom of *L. reclusa*.

8. Dermonecrosis in Rabbits

The dermonecrotic activity was assessed in rabbits and determined as described by Furlanetto et al. (1962a, b).

Different concentrations of the venom were used; they were diluted in 0.2 mL of PBS buffer, pH 7.4, or in 0.2 mL of ammonium acetate 20 mM, pH 4.7. These were intradermically injected into the backs of two rabbits.

In order to better illustrate this invention and its use, the following specific examples are provided to help the reader better understand the different aspects of the practice of this invention. Since these specific examples are merely illustrative, in no case should the following descriptions be considered to limit the scope of this invention:

Example 1

Biochemical Characterization of the Venom of *Loxosceles boneti*

Figure 2:
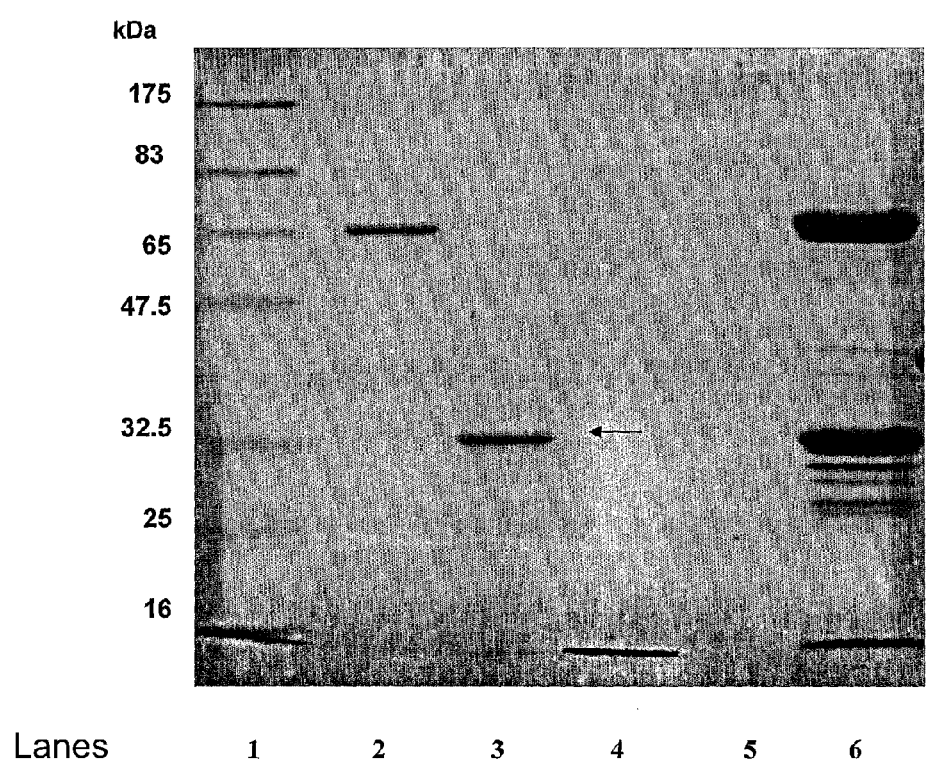
FIG. 2. Analysis through SDS-PAGE of the fractions obtained by gel chromatography. 1) Molecular weight markers. 2) Fraction I (2.24 µg). 3) Fraction II (3.84 µg). 4) Fraction III (1.44 µg). 5) Fraction IV (8 µg). 6) Lysate of *L. boneti* glands (28 µg).
Figure 3:
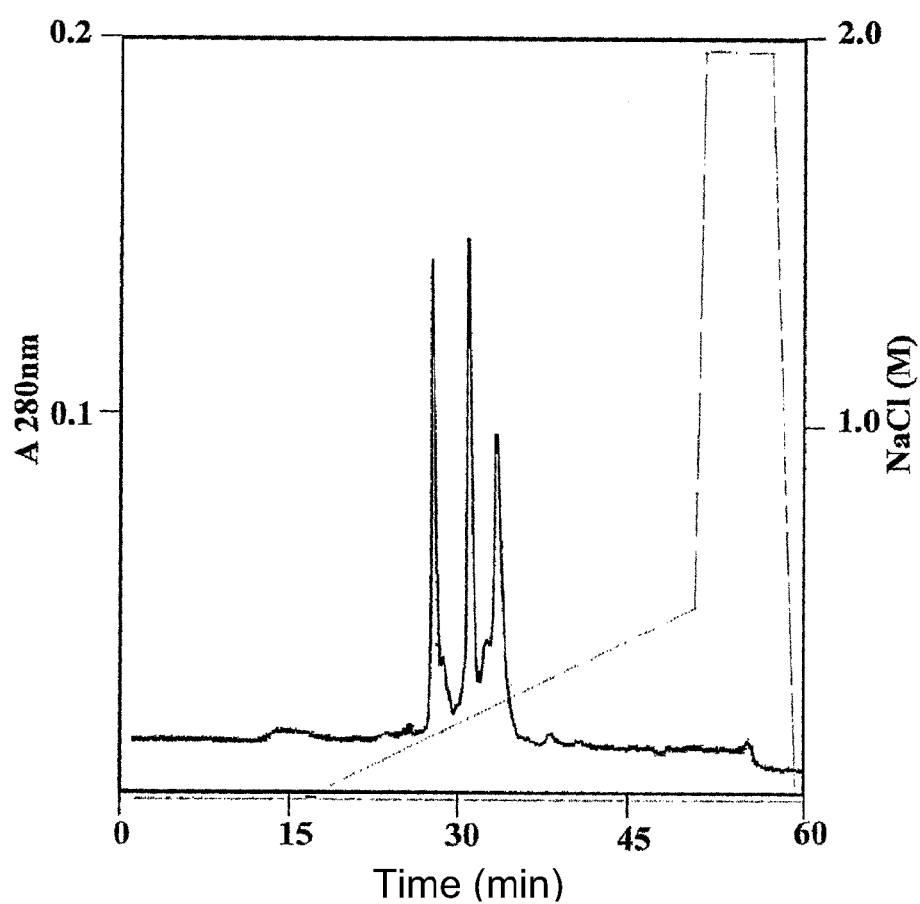
FIG. 3. Results of Cationic Exchange Chromatography for fraction II of *L. boneti*. Each peak represents an isoform. The arrows show other possible isoforms found in lesser amounts within fraction II. The column was of the Mono S type. The column was 5 cm long by 0.5 cm in diameter. The flow rate was 1 mL/min. Sensitivity was of 0.2 AU. The buffer used was 20 mM ammonium acetate pH 4.7, using a gradient of 0-2 M NaCl. The plotting rate was of 15 cm/hr.

To characterize the venom of the *Loxosceles boneti* spider, which is found in Mexico, particularly in the states of Guerrero, Puebla and Morelos, an extract of the glands of the spider was obtained. The extract was lyophilized and reconstituted in ammonium acetate 20 mM pH 4.7; the formation of precipitate was observed. An SDS-PAGE analysis (reducing conditions) showed that the protein of interest was primarily preserved in the supernatant, with which we continued to work. It was separated by molecular exclusion gel chromatography, and 4 main peaks were observed. (FIG. 1). Correspondingly, the samples were separated into 4 fractions, with fraction II containing the protein of approximately 32 KDa, which would presumably be sphingomyelinase (FIG. 2). This fraction II was characterized by ion-exchange chromatography by FPLC to search for possible isoforms, as in the reported cases of *L. reclusa* and *L. intermedia*. Three main peaks corresponding to isoforms I, II and III (FIG. 3) were obtained. Of these, only isoforms I and II showed proven dermonecrotic activity on the skin of rabbits, as described by Furlanetto et al. (1962a, b). The sphingomyelinase activity of fraction II (which comprises the 3 isoforms) was 25 U/mg. Each of the three separated isoforms was dried by centrifugation in SAVANT and then sequenced in an automated Beckman LF3000 apparatus, using Edman's chemistry (Walsh et al., 1981). From isoform I, the first 35 amino acids (SEQ. ID. NO:1) were sequenced; from isoform II, the first 33 (SEQ. ID. NO:2), and from isoform III, the first 22 (SEQ. ID. NO:3). The enzymatic activity for isoform I was 30.5 U/mg; for isoform II, it was 9.5 U/mg, and for isoform III, 0 U/mg.

Example 2

Generation of Polyclonal Antibodies in Mammals Against *L. boneti* Venom and Cross-Reaction with *L. recluse* Venom To generate antivenom antibodies for *L. boneti*, 2 rabbits were inoculated in a 13-inoculation plan. In the first 9 inoculations, the gland extract of *L. boneti* was administered in increasing amounts from 20 to 250 μg, while in the remaining inoculations, 60, 80 and 100 μg of fraction II (mixture of the 3 isoforms), obtained from the molecular exclusion gel chromatography, were administered. Inoculations were performed every 10 days. A volume of 1 mL (in PBS) with incomplete Freund's adjuvant was injected intradermically in all of the cases except for the first, in which complete Freund's adjuvant was injected.

Figure 4:
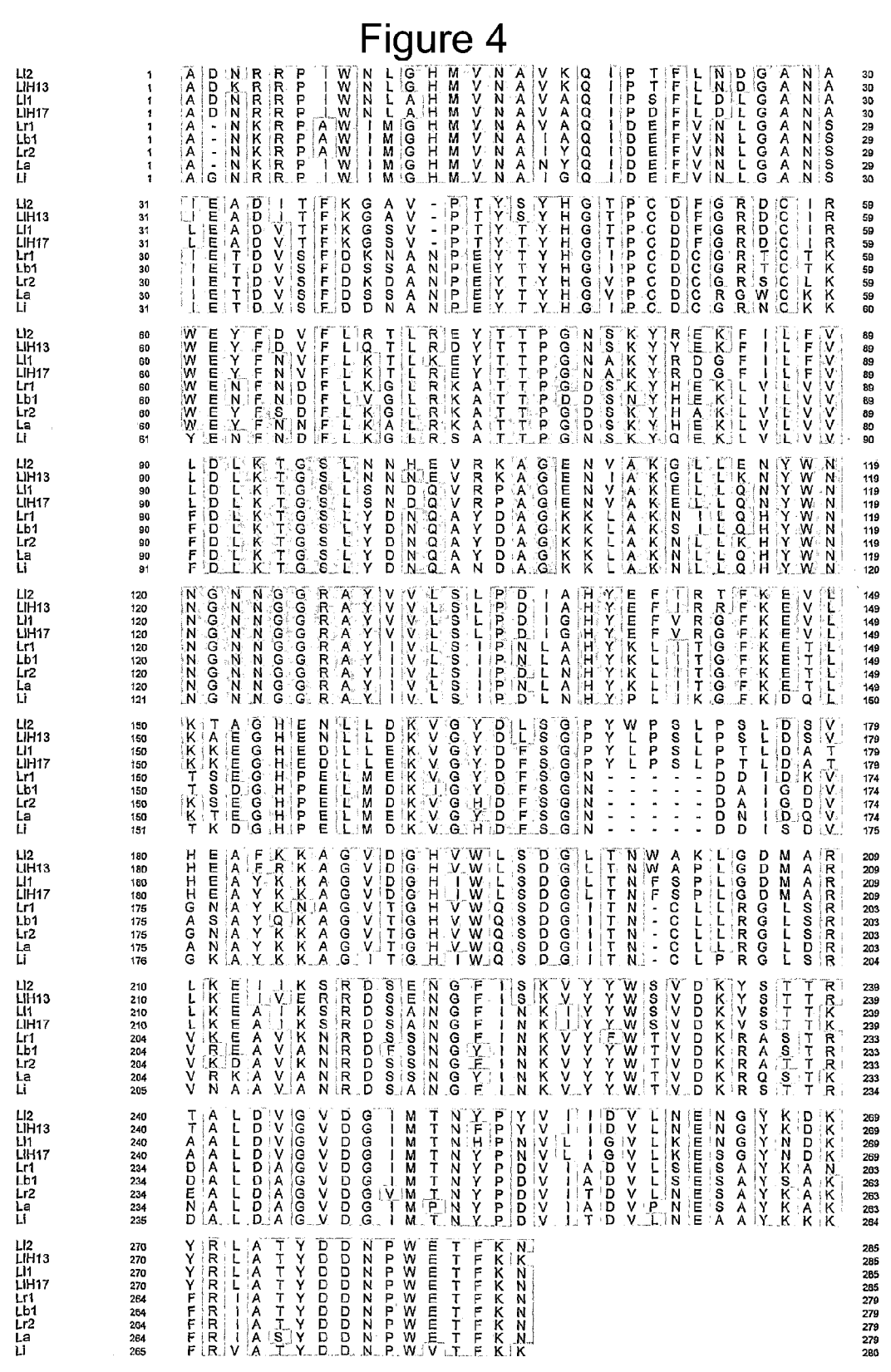

The sera obtained were titrated, obtaining titers of up to 30,000. In cross-reactions with the venom of *L. reclusa*, the titers were up to 23,000. FIG. 4 shows a Western Blot of the venom of *L. reclusa* and *L. boneti* (separated by SDS-PAGE) revealed with the anti-*L. boneti* serum, where the affinity towards the 32.5 KDa component of both venoms is clearly shown.

Example 3

Isolation of Partial Clones of the Necrotoxins of *L. boneti*

To isolate the clones of the necrotoxins, the RNAm of the venom glands of spiders of each species was isolated using the TRIZOL method (Gibco), following the protocol of the manufacturer. The kit 3' RACE (Gibco) was used to synthesize the first chain. 2 μL of the total RNAm (approximately 500 mg) extracted from glands, 4 μL of water, and 1 μL (10 pmoles) of the Adapter Primer (AP) oligonucleotide, which comprises a tail of poly Ts (SEQ.ID. NO:4), were incubated for denaturalization at 7° C. for 10 min and cooled immediately in ice, 2 μL of PCR 10× buffer, 1 μL of dNTPs (10 mM), 2 μL of MgCl2 (25 mM) and 2 μL of DTT (0.1 M) were added, preincubating for 2-4 min at 42° C. 1 μL of Reverse Transcriptase Superscript (Invitrogen) was added immediately; it was mixed and incubated for 50 min at 42° C. The enzyme was inactivated by incubation for 15 min at 70° C., and the mixtures were immediately cooled in ice for 1 minute. 1 μL of RNAsa H was added and incubated for 20 min at 37° C. and stored at −80° C.

For the polymerase chain reaction (PCR), a sample of the first chain reaction (2 μL) was taken, and to it were added a buffer of PCR 10× $Mg^{2+}$ (100 mM TRIS-HCl pH8.3, 500 mM KCl 15 mM $MgCl_2$), 200 μM dNTPs, 20 pmoles of the direct oligonucleotide (at 5'-3' sense), 20 pmoles of the reverse oligonucleotide (at 3'-5' sense) AUAP (GIBCO) (SEQ.ID. NO:5) and two units of Taq DNA Polymerase (ROCHE) in a final volume of 50 μL. The reaction was performed using a Perking Elmer 9600 thermocyclator with the following protocol: Incubation of the mixture for 3 min. at 94° C., followed by 25 cycles of three incubation steps: 1 min at 94° C., 90 sec at 48° C. and 2 min at 72° C. The Taq DNA polymerase binds to the 3' extremes, a useful A to hybridize with the T of the 5' extremes of the linearized cloning vector pCR 2.1-TOPO (3.9 Kb).

For *L. boneti*, 2 oligonucleotides were designed based on the amino acidic sequence determined common to isoforms I and II, the oligo Lb1 (SEQ. ID. NO:6) corresponding to the sequence of amino acids 5 to 10 of the amino terminus of isoforms I and II, and the Lb-nested oligo (SEQ.ID.NO:7), which comprises the last base of aa 7, and those from 8 to 12, and the first two bases of aa 13. The first was used for the PCR reaction while the second was used for a confirmatory PCR. In both cases, the commercial AUAP oligo (GIBCO) (SEQ ID NO:5), which recognizes specifically the sequence of the AP oligo of the same company, was used The products of the PCR were purified in an gel extraction kit (ROCHE), following the directions of the manufacturer. They were afterwards hybridized with (and bound to) to the pCR 2.1-TOPO (3.9 Kb) (Invitrogen) cloning vector linearized by the TOPO isomerase, which shows a salient T in both chains, obtaining the plasmid with the insert (product of PCR 30). These constructions were used to transform the cells of *E. coli* XL1 blue strain. The selection of the clones that comprised an insert was performed by plating the transforming cells in Petri dishes with LB/agar with ampicillin in the presence of X-Gal, selecting the white colonies to amplify the plasmids. Thirteen positive colonies were obtained.

Of the 13 positive colonies, only 7 contained an insert of the correct size. The plasmidic DNAs were sequenced in both chains using fluorescent nucleotides in a Perkin Elmer Applied Biosystems apparatus (Foster City, Calif., USA), as described by the manufacturer. Of the 7 positive clones, one was selected for having the most clearly and unequivocally identified sequence, clone 30-8, with an approximate size of 900 pb.

Example 4

Expression of the Partial Clone of *L. boneti*

In order to be able to express the recombinant protein obtained in the previous example, the cDNA was subcloned in the pTrcHIS-TOPO (INVITROGEN) expression vector. With the purpose of placing the gene in phase in the plasmid, 2 oligonucleotides were designed: the direct one, incomplete Lb5' (SEQ.ID.NO:22), from the codifying sequences of amino acids 5 to 9 of the amino terminus of isoforms I and II (the first 5 of the insert cloned in the previous step), plus the recognizing site for the enzyme BamHI and 3 more bases so that the enzyme binds; and the reverse oligo, Lb3'Sal I (SEQ.ID.NO:9), from the codifying sequence of the aa 275 and 279 (the last 5 of the carboxyl terminus of *L. boneti*'s sphingomyelinase D), plus the terminus codon, plus the recognizing site of the enzyme Sal O and 4 more bases to bind the enzyme. With the plasmid of clone 30-8 as a template and using the designed direct and reverse oligos as primers, a PCR reaction was performed obtaining a DNA fragment that comprises the codifying sequence of the recombinant protein with the 5 to 279 amino acids of the sphingomyelinase of *L. boneti*, with a BamH I cut site in the 5' terminus, and a Sal I cut site in the 3' terminus.

Both the pTrcHIS-TOPO expression vector and the above mentioned PCR product were digested with the BamH I and Sal I enzymes and bound to obtain the pTrcHIS-TOPO 30-8 plasmid, being transformed in electro-competent cells of *E. coli* XL1 blue. Three (3) positive colonies that carried the pTrcHIS-TOPO 30-8 plasmid; they had an insert of the correct size (as observed in a gel, after releasing the insert by digesting the plasmid with BamH I and Sal I) and they were obtained and confirmed by sequencing.

To express the recombinant protein, each of the 3 colonies obtained was cultured in 3 ml, of LB medium in the presence of ampicillin 100 µg/mL at 37° C. overnight with stirring, afterwards they were transferred to a 500-mL LB flask with ampicillin. Once the culture reached an optical density of 0.6 $OD_{600}$, expression was induced with 1 mM IPTG for 3 hours at 37° C. with stirring. The cells were harvested by centrifugation (8,000 rpm, 15 min) and resuspended in 5 mL of A buffer (NaH2PO4 100 mM, TRIS-HCl 10 mM pH 8 and Guanidinium Chloride 6M) and sonicated afterwards for 6 cycles of 30 sec each with intervals of 1 min in ice. Then, it was centrifuged for 25 min at 10,000 rpm. The supernatat was run through a nickel (Ni-NTA agarose) (Qiagen) column to purify the protein. Once the purification was concluded, it was dialized against PBS to eliminate the guanidinium chloride, but the protein precipitated. The precipitated protein was quantified by BCA (PIERCE), but when tested as an immunogen in rabbits, it didn't yield good results. Based on this, we decided to plicate the protein in vitro.

To plicate the protein in vitro, it was solubilized by placing it in the presence of 5M of guanidinium chloride plus 30 M of DTT for 2 hours at room temperature. After this time, the protein was dialyzed against a solution with 2M of guanidinium chloride, 4 mM reduced glutathione (GSH), and 2 mM of oxidized glutathione (GSSG) in PBS 1× pH 47.4, for 1 hour. These dialysis were repeated with decreasing concentrations of guanidinium chloride, keeping those of GSH and GSSG constant, except in the last dialysis step in which they were eliminated from the solution; the protein remained in PBS 1× pH 7.4, recovering 80% of the protein in a soluble form. The solubilized protein lacked sphingomyelinase and dermonecrotic activity, and the antibodies generated in rabbits with this recombinant protein were able to recognize the recombinant protein itself and the dermonecrotic component of the whole venom detected by Western Blot; however, they were unable to neutralize the toxicity of said venom.

Example 5

Isolation of the Complete Clone with Complete *L. boneti* Sphingomyelinase D

In order to obtain a codifying sequence of the complete sphingomyelinase D of *L. boneti* (i.e., from the first amino acid of the amino terminus region up to the last in the carboxyl terminus region), we designed oligonucleotide Lb5'BAM H1 (SEQ.ID.NO:8), which also includes the necessary sequence for the Bam H1 site, the codifying codons of the first 4 aa of the amino terminus of *L. boneti* sphingomyelinase D, plus the next 5 amino acids already present in the original product of the PCR obtained from the 30-8 clone. A PCR reaction was carried out using the pTrcHIS-TOPO 30-8 plasmid as a template and the LB5'BamH1 oligo as direct primer and the same Lb3'Sal I oligo (SEQ.ID.NO:9) as reverse primer, obtaining a DNA fragment that comprises the complete codifying sequence of *L. boneti*'s sphingomyelinase, flanked by the cut sites of BamH I and Sal I. This fragment was cloned in the TOPO 2.1 (3.9 Kb) plasmid, transforming competent cells of *E. coli* XL1 blue; 4 positive colonies were obtained, of which the nucleotidic sequence of the insert was proven by sequencing. A larger amount of plasmid was produced, and the insert, which comprises the complete codifying gene (SEQ. ID. NO: 10) of the active recombinant protein SMDrLb (SEQ. ID. NO: 11), was released by digestion with the Bam HI and Sal I enzymes. The insert was purified using a purification kit (ROCHE) and bound to the pQE30 vector, previously digested with the same restriction enzymes, obtaining vector PQE30Lb-8e3.1.

Example 6

Expression of the Complete SMDrLb Clone

The product of binding with the plasmid PQE30Lb-8c3.1 was used to transform competent cells of *E. coli* BL21, which, when plated, produced 3 positive clones, confirming the presence of he DNA fragment that comprises the complete codifying sequence of *L. boneti's* sphingomyelinase D, as could be corroborated by restriction analysis with Bam HI and Sal I enzymes.

The clone used for the expression was called PQE30Lb-8c3.1. For that purpose, it was cultured at 37° C. in LB plus ampicillin up to an OD of 0.6; it was later induced with 1 mM of IPTG for 3 hours. Again, the protein was expressed in considerable amounts, but in inclusion bodies, whose sphingomyelinase D activity was negligible.

Example 7

Controlled Expression of the Complete Clone of *L. boneti's* Sphingomyelinase D

In order to control the expression level of the recombinant SMDrLb protein, the clone PQE30Lb-8c3.1 was incubated in 50 mL of LB with ampicillin at 37° C. overnight; the cells were transferred to a flask with IL of the same medium—Once an $OD_{600}$ of 0.6 was reached, the culture was induced with IPTG (0.1 mM), and it was incubated for 16 hours at a lower temperature (20-22° C.) with stirring. The cells were recovered by centrifugation (10 min at 8,000 rpm). The cell package was resuspended in 20 mL of PBS, sonicated for 6 cycles of 30 seconds at intervals of 1 min in ice, and centrifuged again for 25 min at 10,000 rpm. A protein with the expected molecular weight (32 Kda) was found both in the supernatant and in the pellet The soluble recombinant protein was purified by running the supernatant through an NiTA (nickel tri-nitrile-acetic, QIAGEN) column, where the recombinant protein attaches to the metal due to high affinity of the 6 histidine tail. It was subsequently washed with 15 volumes of PBS and with volumes of PBS plus imidazole 25 mM, and finally eluted the recombinant protein with PBS plus 250 mM of imidazole. The elusion was collected and dialyzed against PBS to eliminate the imidazole that was still present. The sphingomyelinase activity was measured and turned out to be 31.5 U/mg, i.e., practically the same as the activity found for the native isoform 1.

Example 8

Production of Neutralizing Antibodies from the Active Recombinant Protein SMDrLb With the active recombinant soluble protein SMDrLb produced as set forth in Example 7, two 3.5-Kg New Zealand rabbits were inoculated with a scheme of 8 inoculations at 10-day intervals, with increasing amounts of the recombinant protein, from 30 to 100 μg/rabbit of (active) soluble recombinant protein in PBS. Inoculations were applied intradermically in a final volume of 1 mL, with 0.5 mL of Freund's adjuvant, complete for the first inoculation and incomplete for the subsequent inoculations.

Ten days after the eighth inoculation, the antibody titre was measured, and it was 22,800 for one rabbit and 29,300 for the other. The rabbits were bled to death, and the serum of both rabbits was separated and mixed (50/50% in volume).

To determine the median effective dose (ED50) of the serum mixture, 3 challenges were performed with different amounts of the same recombinant protein SMDrLb, 7.8, 15.45 y 18.1 μg/mouse. For that purpose, groups of 4 Balb-C mice weighing 18-20 g were used; they were injected with a pre-incubated (30 min at 37° C.) mixture of the SMDrLb protein with increasing amounts (from 100-200 μL) of the serum mixture of the 2 inoculated rabbits in SS (NaCl 0.15 M), obtaining the following ED50; Mean while in a similar assay, 92 μg of the native venom of pre-incubated *L. boneti* with increasing amounts of the homologous serum (anti-SMDLrLb) were applied, thus obtaining an ED50 of 149.6 μg per mouse, which for the 92 μg are equivalent to 3LD50.

| SMDrLb quantity | ED50 |
|---|---|
| 7.8 μg | 154.6 μl |
| 15.5 μg | 258.7 μl |
| 18.1 μg | 276.5 μl |

The calculations were made using the GraphPad Prism software (Version 2; GraphPad Software. Inc, San Diego, Calif.).

Example 9

Isolation of Complete Clones of *L. recluse* Sphingomyelinase D

To isolate the clones of the necrotoxins, the total RNA of the venom glands of spiders was isolated using the TRIZOL reagent method (Gibco), following the protocol of the manufacturer. Kit 3' RACE (Gibco) was used to synthesize the first chain. 2 μL of the total RNA (approximately 500 ng) extracted from glands, 4 μL of water, and 1 μL (10 pmoles) of the Adapter Primer (AP) oligonucleotide, which comprises a tail of poly-Ts (SEQ.ID. NO:4), were incubated for denaturalization at 70° C. for 10 min and cooled immediately in ice. 2 μL of PCR 10× buffer, 1 μL of dNTPs (10 mM), 2 μL of MgCl2 (25 mM) and 2 μL of DTT (0.1 M) were added, preincubating them for 2-4 min at 42° C. 1 μL of Reverse Transcriptase (Invitrogen) was added immediately; it was mixed and incubated for 50 min at 42° C. The enzyme was inactivated by incubation for 15 min at 70° C., and the compound was immediately cooled in ice for 1 minute. 1 μL of RNAsa H was added, and it was incubated for 20 min at 37° C. and stored at −80° C.

In order to do the polymerase chain reaction (PCR), a sample was taken (2 μL) of the reaction made with the first chain and it was added PCR buffer 10× $Mg^2$ (100 mM TRIS-HCL pH 8.3, 500 mM KCl 15 mM $MgCl_2$), 200 μM dNTPs, 20 μmoles of the direct oligonucleotide (in the 5'-3' sense). In this case we used the same LB5'Bam H1 oligonucleotide (SEQ. ID. NO:8) which includes in addition to the necessary sequence for the Bam H1 site, the codifying codons of the first 9 AAs of the amino terminus of *L. reclusa* sphingomyelinase D. 20 μmoles of the reverse oligonucleotide (in the 3'-5' sense), the reverse Lb3?Sal I (SEQ. ID. NO: 9) oligo and two units of the Taq DNA Polymerase (New England Biolabs, Beverly, Mass., USA) in a final volume of 50 μL. The reaction was performed using a Perkin Elmer 9600 thermocyclator with the following protocol: Incubation of the mixture for 3 min, at 94° C., followed by 25 cycles of three incubation steps: 1 min at 94° C., 90 sec at 48° C., and 2 min at 72° C. At the end, a step of 10 min at 72° C. The Taq DNA polymerase binds to the 3' extremes, a useful A to hybridize with the T of the 5' extremes of the cloning vector pCR 2.1 TOPO (3.9 Kb).

The products of the PCR were purified in an extraction kit (ROCHE), following the directions of the manufacturer. They were subsequently hybridized with (bound to) the pCR 2.1-TOPO (3.9 Kb) (Invitrogen) cloning vector linearized by the TOPO isomerase, which shows a salient T in both chains, obtaining the plasmids pCR 2.1-TOPO Lr1 and pCR 2.1-

TOPO Lr2 that comprise the insert produced by PCR, Lr1 and Lr2, respectively. These constructions were used to transform the cells of E. coli XL1 blue strain. The selection of the clones that comprised an insert was performed by plating the transforming cells in Petri dishes with LB/agar with ampiciline in the presence of X-Gal, selecting the white colonies to amplify the plasmids. Five positive colonies were obtained.

Of the 5 positive colonies, only 2 (Lr1 and Lr2) contained an insert of the correct size. The plasmidic DNAs were sequenced in both chains using fluorescent nucleotides in a Perkin Elmer Applied Biosystems apparatus (Foster City, Calif., USA), as described by the manufacturer. The 2 positive clones were selected because they had the sequence most clearly identified as sphingomyelinase D and with variations among them (90% identity). Both clones, with an approximate size of 900 pb, comprised respectively the complete codifying sequences of two isoforms of the sphingomyelinase D of L. reclusa (SEQ. ID. No: 12 and SEQ. ID. No: 14) whereas the codified proteins (SMDrLr1 and SMDrLr2) had the amino acidic sequences SEQ.ID. No: 13 y SEQ.ID. No: 15. For each of them, the insert, which comprises the gene of the corresponding SMDrLr, was released by digestion with the enzymes Bam H1 and Sal I. Each insert was purified using a purification kit (ROCHE) and bound to the pQE30 vector, previously digested with the same restriction enzymes, obtaining vectors PQE30Lr1 and PQE30Lr2.

Example 10

Controlled Expression of the Complete Clones of SMDrLr

In order to control the expression level of the recombinant protein (both SMDLr1 and SMDrLr2), the cells of E. coli BL21 transformed with vector PQE30Lr1 or PQE30Lr2 were incubated in 3 mL of LB with ampicillin at 37° C. overnight; they were transferred to a flask with 100 mL of the same medium containing 1 mM of IPTG, and they were incubated for 16 hours at a temperature of 20-22° C. The cells were recovered by centrifugation (10 min at 10,000 rpm). The cell package was resuspended in 5 mL of PBS, sonicated for 6 cycles of 30 seconds at intervals of 1 min in ice, and centrifuged again for 25 min at 10,000 rpm. A protein with the expected molecular weight. (32 Kda) was found both in the supernatant and in the pellet.

The soluble recombinant proteins SMDrLr1 and SMDrLr2 were purified by running the supernatant through a NiTA (nickel tri-nitrile-acetic, QIAGEN) column, where the recombinant protein attaches to metal due to the high affinity of the 6 histidine tail. They were subsequently washed with 10 volumes of PBS and with 10 volumes of PBS plus imidazole 25 mM, and finally eluting the recombinant protein with PBS plus 250 mM of imidazole. The elusion was collected and dialyzed against PBS to eliminate the imidazole that was present. The sphingomyelinase activity was measured and turned out to be 27.2 U/mg for SMDrLr1, i.e., practically the same as the activity found for the native isoform and 11.47 U/mg for SMDrLr2.

Example 11

Production of Neutralizing Antibodies from the Active Recombinant Protein SMDrLr1

One of the recombinant proteins was selected: SMDrLr1. With the protein produced as set forth in Example 10, two 3.5-Kg New Zealand rabbits were inoculated with a scheme of 8 inoculations at 10-day intervals with increasing amounts of the recombinant protein, from 30 to 100 µg/rabbit of (active) soluble recombinant protein in PBS. Inoculations were applied intradermically in a final volume of 1 mL, with 0.5 mL of Freund's adjuvant, complete for the first inoculation and incomplete for the subsequent inoculations.

The antibody titre was measured; it was 26,000 for one rabbit and 33,000 for the other one. The rabbits were bled to death, and the serum of both rabbits was separated and mixed (50/50% in volume).

To determine the median effective dose (ED50) of the serum mixture, groups of 4 Balb-C mice weighing 18-20 g were used; they were injected with a pre-incubated (30 min at 37° C.) mixture of the SMDrLr1 toxin with increasing amounts of the serum mixture of the 2 inoculated rabbits, in SS (NaCl 0.15 M).

The median effective dose of the anti-SMDrLr1 antivenom against the active recombinant protein proved to be 165 µL for mice, with 12 µg of protein. The calculations were made using the GraphPad Prism software (Version 2; GraphPad Software, Inc, San Diego, Calif.); Mean while, in a similar assay, 12 µg of the native venom of L. reclusa pre-incubated with increasing quantities of the homologous serum (anti-SMDrLr1), were applied to each mouse, and was found an ED50 of 175 µL per mouse with 12 µg of homologous venom Example 12

Isolation of the Complete Clones of the Complete Sphingomyelinase D of L. laeta

We proceeded as in Example 9, but using venom glands from L. laeta as the source of transcripts. The direct oligo L15'BamHI (SEQ.ID.NO:16) and the reverse oligo L13'Sal I (SEQ.ID.NO:17) were used for the PCR. These were designed based on the sequences reported for the Brazilian variety (Fernandes Pedrosa, et al., 2002), whose products were purified and selected in the same way, obtaining 2 clones with a clearly identified sequence and with variations between them (88% of identity); these products comprised, respectively, the complete codifying sequences of two isoforms of the sphingomyelinase D of L. laeta (SEQ. ID. No: 18 and SEQ. ID. No: 20), while the codified proteins (SMDrLl1 And SMDrLl2) had the amino acidic sequences SEQ.ID. No: 19 and SEQ.ID. No: 21. Finally, they were subclonated in the plasmid pQE30, obtaining vectors PQE30Ll1 and PQE30L12, ready for expression.

Example 13

Controlled Expression of the Complete SMDrLl1 Clone

Two clones, SMDrLl1 and SMDrLl2, were selected for expression. To achieve a controlled expression, so as to prevent all of the recombinant protein from being expressed as inclusion bodies, we proceeded as in Example 10, but transforming the cells with vectors PQE30Ll1 and PQE30Lr2. The recombinant proteins thus produced had an activity of 58.43 U/mg for SMDrLl1 and of 252 U/mg for SMDrLl2.

Example 14

Production of Neutralizing Antibodies from the Active Recombinant Protein SMDrLl1

We proceeded in a manner similar to Example 11, but using the SMDrLl1 protein from Example 13 to inoculate the animals. The titers reached values of up to 34,300, and an ED50 of 200 μL per mouse with 12 μg of SMDrL11 and of 225 μL per mouse with 12 μg of the homologous venom, was found.

Example 15

Cross-Protection Assays

Cross-protection assays were successfully carried out challenging mice with 12 μg of *L. boneti* venom or SMDrLb protein; we found that an ED50 of 112 μL of rabbit anti-SMDrLr serum per mouse, and 200 μL of the same per mouse were enough to neutralize 100% of the toxic effect of the venom. In the same way, mice were challenged with 12 μg of native venom of *L. reclusa* or SMDrLr1 protein, and it was found that between 160 and 200 μL of rabbit anti-SMDrLb serum were enough to neutralize its toxic effect.

Example 16

Subcloning of Clones Lb1, Lr1, Lr2, and L12 with Histidines in the Carboxyl Position To demonstrate that the inclusion of the histidine tail in the amino terminus of the recombinant SMD proteins object of this invention (amino versions) has no significant effect on the effectiveness of the protein, some of the clones: Lb1, Lr1, Lr2 and L12 were subcloned in the pQE60 plasmid that adds the histidine tail to the carboxyl terminus instead of the amino terminus. For this purpose, the same oligos were used: Lb5'Bam H1 (for Lb1, Lr1 and Lr2) and L15'Bam H1 (for L12) as direct oligos, and Lb3' Bgl II (SEQ.ID.NO: 23) and L13' Bgl II (SEQ.ID.NO: 24), respectively, as reverse oligos. The constructions were expressed in a controlled manner in strains of *E. coli* BL21 in the same way as in Examples 7, 10, and 13. The recombinant proteins thus produced (carboxyl version), presented essentially the same SMD activities as the amino versions.

Example 17

Production of Antibodies in Horses, Against a Mixture of Several of the Recombinant Proteins of the 3 *Loxosceles* Species To further illustrate the ability of the recombinant proteins of this invention to generate neutralizing antibodies in vertebrates, particularly in mammals, this time a horse was selected for the generation of antibodies. At the same time, to illustrate the possibility of using an immunogenic composition that comprises more than one of the recombinant proteins of this invention, 4 of them which were considered sufficiently representative were selected to neutralize the venoms of at least 3 species of the *Loxosceles* spider, some in their amino version and others in their carboxyl version. In this way, the immunogenic composition was composed of 2 parts of SMDrLr1 (amino version or SMDrLr1-NH2), 2 parts of SMDrLb (carboxyl version or SMDrLb-COOH), 1 part of SMDrL11 (amino version or SMDrL11-NH2) and 1 part of SMDrL12 (carboxyl version or SMDrL12-COOH).

Five horses that had never been immunized or had never had contact with any antigen related to the *Loxosceles* spider were selected and inoculated with the immunogenic composition mentioned in the previous paragraph. The inoculation was carried out over a period of 9 months, starting with a dose of 2.5 μg of the recombinant toxin mixture and ending with 250 μg. The inoculations were performed at intervals of two weeks, and Freund's adjuvant and alumina were used, alternately, as adjuvants. The inoculation was performed subcutaneously. Blood samples were taken from the horses at one-month intervals in order to measure the antibody titers by immunoenzymatic assay.

The horses were bled at the end of the nine-month period, and the plasma was mixed and processed to produce F(ab')2 fragments by digestion with the pepsin enzyme and its subsequent purification. The median effective dose of the F(ab')2 fragments was determined in a similar way to that described in Example 8. Fourteen (14) groups of 5 Balb-C mice weighing 18-20 g were used. Two groups were immunized (one control and one treated with F(ab')2 fragments) for each of the following recombinant proteins (recombinant toxins) or venoms: SMDrLr1-NH2, SM DrLb-COOH, SMDrL11-NH2, SMDrL12-COOH, venom of *L. boneti*, venom of *L. reclusa*, and venom of *L. laeta* For this purpose, they were injected with a pre-incubated mixture (30 min at 37° C.) of 5LD50 of the recombinant protein or venom, either with increasing amounts (from 100-200 μL) of the F(ab')2 fragments obtained, in SS (NaCl 0.15 M) for the treatment groups, or with SS only for the control groups. From the ED50s determined by using the above-mentioned GraphPad Prism software, the amounts of neutralized toxin or venom per 1 mg of F(ab')2 fragments (neutralizing ability) were calculated, and they are shown below:

| Recombinant toxin or natural venom | μg of toxin or venom neutralized per mg of F(ab')2 fragments |
| --- | --- |
| SMDrLb-COOH | 251 |
| SMDrLr1-NH2 | 235 |
| SMDrL11-NH2 | 55 |
| SMDrL12-COOH | 105 |
| *L. boneti* venom | 629 |
| *L. reclusa* venom | 587 |
| *L. laeta* venom | 394 |

Example 18

Obtaining Toxoids of SMDrLb

Based on the recently reported (Murakami et al., 2005) identification of the catalytic center of one of the isoforms of the sphingomyelinase D of *L. laeta*, we decided to perform mutagenesis on the codifying DNA of SMDrLb (SEQ. ID.NO:10), a mutant in the codifying codon of the histidine residue in position 11, and the other one in the codifying codon for the glutamic acid residue in position 31, both counted in the mature protein. The first mutant obtained, designated SMDrLb(H11K), consisted of substituting the histidine in position 11 for a lysine; it has a SEQ.ID.NO:27 for its codifying sequence and SEQ.ID.NO:28 for the mature expressed protein. The second mutant, designated SMDrLb (E31K), consisted of substituting the glutamic acid in position 31 for a lysine; it has a SEQ.ID.NO:29 for its codifying sequence and a SEQ.ID.NO:30 for the expressed mature protein.

To obtain the mutants, clone PQE30Lb-8c3.1 and the QuickChange directed mutagenesis kit (QuickChange Site-Directed Mutagenesis Kit) (Stratagene, La Jolla, Calif., USA) were used, following the protocol recommended by the company (Papworth, C. et al., 1996).

The two mutants, SMDrLb(H11K) and SMDrLb(E31K), incorporated in the pQE30 vector were isolated and expressed in a controlled way in the *E. coli* BL21 strain, in a way similar to the one described for SMDrLb in Example 7.

Both proteins were successfully expressed in a soluble form (and part of them as inclusion bodies). Their sphingomyelinase D enzymatic activity was analyzed by the method described previously, and its result was null. Additionally, dermonecrosis tests were performed on rabbits, which demonstrated that they lack this effect.

To determine if these enzymatically inactive and non-dermonecrotic versions expressed in a soluble form were capable of generating neutralizing antibodies for the active SMDrLb or the venom of *L. boneti*, for each of the mutants, two 3.5-kg New-Zealand rabbits were inoculated with a scheme of 8 inoculations, at 10-day intervals, with increasing amounts of the recombinant protein, from 30 to 100 µg/rabbit of recombinant soluble protein (inactive) in PBS. Inoculations were performed intradermically in a final volume of 1 mL, with 0.5 mL of Freund's adjuvant, complete for the first inoculation and incomplete for the subsequent inoculations.

In both cases, titers that varied from between 25,200 and 31,500 were obtained. For each case, the rabbits were bled to death, and the serum of both rabbits was separated and mixed (50/50% in volume).

To determine the median effective dose, ED50, of the serum mixture of each case, groups 4 of Balb-C mice weighing 18-20 g were used. They were injected with a pre-incubated (30 min at 37° C.) mixture of 12 µg of SMDrLb toxin with increasing amounts of the serum mixture of the 2 inoculated rabbits, in SS (NaCl 0.5 M).

From the ED50s determined using the GraphPad Prism software, the amounts of neutralized toxin or venom per 1 mL of each of the sera (neutralizing ability) were calculated, and they are shown below:

| Recombinant toxin or natural venom | µg of toxin or venom neutralized per mL of serum | |
|---|---|---|
| | anti-SMDrLb(H11K) | anti-SMDrLb(E31K) |
| SMDrLb-COOH | 58.5 | 53.8 |
| *L. boneti* venom | 162.5 | 151.1 |

REFERENCES

Alouf, Ann. Inst. Pasteur/Microbiol. 136B:309 (1985).
Araujo, C. P., Alvarenga, L. M., Mangili, O. C., Kalapoihakis, E., Chavez, O. C., 2003 Protection against dermonecrotic and lethal activities of *Loxosceles intermedia* spider venom by immunization with a fused recombinant protein. *Toxicon*, 41 (3): 261-267.
Audibert, F., Jolivet, M., Chedid, L., Arnon R., and Sela, M., 1982. Successful immunization with a totally synthetic diphtheria vaccine, Proc. Natl. Acad. Sci. USA 79 (16): 5042-5046.
Ayeb and Delori, In: Handbook of Natural Toxins, vol. 2, Insect Poisons, Allergens, and Other Invertebrate Venoms (Anthony T. Tu, Ed.) (Marcel Dekker) (1984) Cap. 18, pp. 607-638.
Barbaro, K. C., Ferreira, M. L., Cardoso, D, F., Eickstedt, V. R. D., Mota, I., 1996[a] identification and neutralization of biological activities in the venoms of *Loxosceles* spiders. Braz. J. Med. Biol. Res. 29(11) 1491-1497 pp.
Barbaro, K. C., Sousa M. V., Morhy, L., Eickstedt, V. R. D., Mota, I. 1996[b]. Compared chemical properties of dermonecrotic and lethal toxins from spiders of the genus *Loxosceles* (Araneae). Journal Protein Chemical. 15 (4), 337-343 pp.
Cevallos, M. A., C. Navarro-Duque, M. Varela-Julia and A. C. Alagón. 1992. Molecular mass determination and assay of venom hyaluronidases by sodium dodecyl sulfate-polyacrilamide gel electrophoresis. Toxicon 30(8), 925-930 pp.
Feitosa, L., Gremski, W., Veiga, S. S., Elias, M. C. Q. B., Graner, E., Mangili, O. C. and Brentani, R. R. 1998. Detection and characterization of metalloproteinases with gelatinolytic, fibronectinolytic and fibrinogenolytic activities in Brown spider (*Loxosceles intermedia*) venom. *Toxicon*, 36(7). 1039-1051.
Fernades Pedrosa, M. F., Junqueira de Azevedo I. L., Goncalves-de-Andrade, R. M., van den Berg, C. W., Rarmos, C. R., Ho, P. L., Tambourgi, D. V. 2002. Molecular cloning and expression of a functional dermonecrotic and haemolytic factor from *Loxosceles laeta* venom. Biochem Biophys. Res Comm. 298 (5), 638-45.
Furlanetto, R. S., Santos, N. P., Navas, J., 1962[a]. Preparacao, purificacao e doseamnento do soro antiloxoscélico. Ciencia e Cultura 14, 254.
Furlanetto, R. S., Bucherl, W., Rosa, R. R, Saliba, F., Navas, J., 1962[b]. Obsercacao dos efeítos do veneno loxoscélico e avaliacao de sua atividade. Ciencia e Cultura 14, 254.
Gatt, S., Dinur, T., Barenhoñz, Y., 1978. A spectrophotometric method for determination of sphingomielynase. Biochim. Biophys. Acta 530, 503-507 pp.
Geren, C. R., Odell G. V. 1984. The biochemistry of spider venoms. In Tu, A. T. (Ed.), Insect Poisons, Allergens, and Other Invertebrate Venoms, Vol. 2. Marcel Dekker, New York, 441-481 pp.
Gerstch, W. J., Ennik, F. 1983. The spider Genus *Loxosceles* in North America, Central America and the West Indie (Araneae, Loxoscelidae). Bull. Amer. Mus. Nat. Hist. USA 175(3): 264-360 pp.
Gomez, H. F., M. J. Miller, M. W. Waggener, H. A. Lankford and S. S. Warren. (2001). Antigenic cross-reactivity of venoms from medically important North American *Loxosceles* spider species. Toxicon 39(7): 991-1002.
Guilherme, P., Fernandes, I., and Barbaro, K. C., 2001. Neutralization of dermonecrotic and lethal activities and differences among 32-35 kDa toxins of medically important *Loxosceles* spider venoms in Brazil revealed by monoclonal antibodies. *Toxicon* 39(9), pp. 1333-1342.
Hoffmann, A. 1976. Relación bibliográfica de las arañas de México (Arachnida: Araneae). Instituto de Biologia, UNAM. Publicaciones especiales. 3: 21-23 pp.
Kalapothakis, E., Araujo, S. C., de Castro, C. S., Mendes, T. M., Gomez M. V., Mangili, O. C., Gubert, I. C., Chavez, O. C. 2002 Molecular cloning, expression and immunological properties of LiD1, a protein from the dermonecrotic family of *Loxosceles intermedia* spider venom. Toxicon, 40 (12): 169-1699.
Kukongviriyapan et al., J. Immunol. Meth. 49:97 (1982).
Lomonte B., Gutierrez, J. M., and Mata, E., 1985. Isolation from a polyvalent antivenom of antibodies to a myotoxin in *Bothrops asper* snake venom. Toxicon 23 (5): 807-813.
Maguire, J. H., Spielman A. Infestaciones por ectoparásitos y mordeduras y picaduras de artódpodos. En: Fauci A. S., Braunwald E., Isseibacher K. J., Wilson J. D., Marlin J. B., Kasper D. L., Hauser S. L., Longo D. L., eds. 1998. Principios de Medicina Inrerna. Vol. II España: McGraw Hill-Interamericana:2906.
Mathews, C. y Holde, K. 1998. Bioquimica. Segunda edición, Editorial Mc-GrawHill Interamericana, España.

Moye De Alba, C. E. Picaduras y mordeduras. En Aguilar C. S., Chevolle R. J., Saucedo J. Kaplan, S. M., Dia A.; Eraña, G. J., eds. 1997. *Manual de Terapeútica Médica y Procedimientos de Urgencias*. México: Mc Craw Hill-Interamericana; 2835 pp.

Murakami, M. T., Fernandes-Pedrosa M. F., Tambourgi V. D. and Arni, R. K. 2005. Structural basis for metal-ion coordination and the catalytic mechanism of sphingomyelinases D. J. Biol. Chem. 280(14): 13,658-13,664.

Papworth, C., Bauer, J. C., Braman, J. and Wrigth, D. A. 1996. Site-directed mutagenesis in one day with >80% efficiency. Strategies 9: 3-4.

pET System Manual. Novagen. 9th Edition. 2000. Pag. 11.

Platnick, N. I. 2000 The World of Spider Catalog. The American Museum of Natural History. http://research.amnh.org/entomology/spiders/

Ramos, R. H., Váquez R. I. 2000. Arañismo ocasionado por especies del Género *Loxosceles*, dentro del apartado Urgencias Médico-quirúrgicas. Revista Educativa pare la Salud. 25-34 pp.

Rosse, W., Flankin, B. H, Anemias hemoliticas y por pérdida aguda de sangre. En: Fauci A S, Braunwald E., Isselbacher. K. J., Wilson J. D., Martin, J. B., Kasper, D. L., Hauser, S. L., Longo D. L., eds. Principios de Medicina Interna. Vol. 1, España: Mc Graw Hill-Interamericana, 1998. 764 pp.

Russell et al., 1985, Preparation Chromatography, Am. J. Trop. Med. Hyg. 34:141-150.

Russell, F. E. 1987. Mordeduras y picaduras venenosas. En: Berkow R., Fletcher A, eds. El Manual Merck. España: Ediciones Doyma, 2835

Sánchez J. 1993. A cien Aññnos de la Zoologia Médica. México. Instituto de Seguridad y Servicios Sociales de los Trabajadores del Estado Tambourgi, D. V., Magnoli, F. C, van den Berg, C. W., Morgan, B. P., de Araujo, P. S., Alves, E. W., Dias Da Silva, W. 1998. Sphingomyelinases in the venom of the spider *Loxosceles intermedia* responsible for both dermonecrosis and complement-depent hemolysis. Biochem. Biophys. Res. Common. 251 (1), 366-373 pp.

Tan, N. H., Ponnundurai, G., 1992. Comparative study of the enzymativ, hemorrhagic, procoagulant an anticoagulant activities of some animal venoms. Comp. Biochem. Physiol. 103C (2). 299-302 pp.

Walsh, K. A., Ericsson, L. H. Parmelle, D. C., Titani, K., 1981. Advances in Protein Sequencing. Ann. Rev. Biochem. 50: 261-284.

Wright, R. P. 1973. Enzymatic characterization of brown recluse spider venom. Bull. Mo Acad. Sci. Supplement 2, 1-94 pp.

Yang, C. C., Lin M. F., and Chang, C. C., 1977. Purification of anticobrotoxin antibody by affinity chromatography. *Toxicon* 15 (1): 51-62

Young, A. R., S. J. Pincus. 2001. Comparison of enzymatic activity from three species of necrotising arachnids in Australia: *Loxosceles rufescens, Badunna insignis* and *Lampona cylindrata*. Toxicon 39(2-3), 391-400 pp.

The following patents or applications are quoted:

Mexican patent application No: 9911191. Alagón, A., L. D. Possani, G. Gurrola, E. Grishin, A. Lipkin, y E. Volynaski. "Inmunógeno, anti-veneno y vacuna contra el veneno de la araña viuda negra".

U.S. Pat. No. 5,904,922. Carroll, S. B. Treatment with polyvalent antivenom containing immunoglobulin which is greater than 50% venom-reactive.

U.S. Pat. No. 5,443,976. Carroll, S. B. Immobilization of *Crotalus atrox* and *Crotalus durissus* terrificus whole venoms on aldehyde-activated agarose.

What is claimed is:

1. A recombinant toxoid selected from the group consisting of SMDrLb1(H11K) and SMDrLb1(E31K), wherein the toxoid has an amino acid sequence as provided in SEQ ID NO: 28 and SEQ ID NO: 30, respectively, the toxoid characterized by being an antigen lacking sphingomyelinase D property, by not being dermonectrotic, and by being able to generate neutralizing antibodies against the venom of *Loxosceles boneti*.

2. A method of neutralizing the venom of *Loxosceles boneti* or for treating the poisoning caused by *Loxosceles boneti* comprising administering a recombinant toxoid selected from the group consisting of SMDrLb1(H11K) and SMDrLb1(E31K) to a patient in need thereof, wherein the toxoid has an amino acid sequence as provided in SEQ ID NO: 28 and SEQ ID NO: 30, respectively, the toxoid characterized by being an antigen lacking sphingomyelinase D property, by not being dermonectrotic, and by being able to generate neutralizing antibodies against the venom of *Loxosceles boneti*.

3. The method according to claim 2, wherein the recombinant toxoid optionally include a histidine tail at the C or N terminus region.

4. A method for obtaining an antivenom to neutralize the venom of *Loxosceles boneti* spiders comprising:
   a. immunizing a non-human, vertebrate animal with an antigen selected from the group consisting of:
      i. SMDrLb1 (H11K), SEQ ID NO: 28;
      ii. SMDrLb1(E31K), SEQ ID NO: 30 and
      iii. a mixture thereof
   b. obtaining serum or plasma from the animal and isolating the polyclonal antibody fraction;
   c. optionally hydrolyzing the polyclonal antibody fraction to obtain an F(ab)$_2$ fragment of the polyclonal antibody;
   d. determining the DE50 of the polyclonal antibody or the F(ab)$_2$ for neutralizing the venom of *Loxosceles boneti* spiders; and
   e. obtaining an effective dose based on the determined DE50.

5. The method according to claim 4, wherein the vertebrate is a mammal.

6. The method according to claim 5, wherein the vertebrate is an equine.

* * * * *

SEQUENCE LISTING

```
<160> NUMBER OF SEQ ID NOS: 30

<210> SEQ ID NO 1
<211> LENGTH: 35
<212> TYPE: PRT
<213> ORGANISM: Loxosceles boneti
<220> FEATURE:
<223> OTHER INFORMATION: Amino-terminal fragment of Sphingomyelinase D,
      isoform I

<400> SEQUENCE: 1

Ala Asn Lys Arg Pro Ala Trp Ile Met Gly His Met Val Asn Ala Ile
1               5                   10                  15

Ala Gln Ile Asp Glu Phe Val Asn Leu Gly Ala Asn Ser Ile Glu Thr
            20                  25                  30

Asp Val Ser
        35

<210> SEQ ID NO 2
<211> LENGTH: 33
<212> TYPE: PRT
<213> ORGANISM: Loxosceles boneti
<220> FEATURE:
<223> OTHER INFORMATION: Amino-Terminal fragment of Sphingomyelinase D,
      isoform II

<400> SEQUENCE: 2

Ala Asn Lys Arg Pro Ala Trp Ile Met Ala His Met Val Asn Ala Val
1               5                   10                  15
```

Ala Gln Ile Asp Glu Phe Val Asn Leu Gly Ala Asn Ser Ile Glu Thr
            20                  25                  30

Asp

<210> SEQ ID NO 3
<211> LENGTH: 25
<212> TYPE: PRT
<213> ORGANISM: Loxosceles boneti
<220> FEATURE:
<223> OTHER INFORMATION: Amino-Terminal fragment of Sphingomyelinase D,
      isoform III

<400> SEQUENCE: 3

Arg Pro Lys Pro Ile Trp Asp Val Ala His Met Val Asn Asp Leu Glu
1               5                   10                  15

Leu Val Asp Glu Tyr Leu Gly Asp Gly
            20                  25

<210> SEQ ID NO 4
<211> LENGTH: 37
<212> TYPE: DNA
<213> ORGANISM: Artificial Sequence
<220> FEATURE:
<223> OTHER INFORMATION: oligonucleotide Adapted Primer

<400> SEQUENCE: 4
ggccacgcgt cgactagtac tttttttttt ttttttt                        37

<210> SEQ ID NO 5
<211> LENGTH: 20
<212> TYPE: DNA
<213> ORGANISM: Artificial Sequence
<220> FEATURE:
<223> OTHER INFORMATION: Oligonucleotide AUAP

<400> SEQUENCE: 5
ggccacgcgt cgactagtac                                           20

<210> SEQ ID NO 6
<211> LENGTH: 17
<212> TYPE: DNA
<213> ORGANISM: Artificial Sequence
<220> FEATURE:
<223> OTHER INFORMATION: Oligonucleotide Lb1
<220> FEATURE:
<221> NAME/KEY: modified_base
<222> LOCATION: (3)..(3)
<223> OTHER INFORMATION: "n" represents inosine
<220> FEATURE:
<221> NAME/KEY: modified_base
<222> LOCATION: (6)..(6)
<223> OTHER INFORMATION: "n" represents inosine

<400> SEQUENCE: 6
ccngcntgga thatggg                                              17

<210> SEQ ID NO 7
<211> LENGTH: 18
<212> TYPE: DNA
<213> ORGANISM: Artificial Sequence
<220> FEATURE:
<223> OTHER INFORMATION: Oligonucleotide Lb-nested
<220> FEATURE:
<221> NAME/KEY: modified_base
<222> LOCATION: (10)..(10)
<223> OTHER INFORMATION: "n" represents inosine

<400> SEQUENCE: 7

```
gathatgggn cayatggt                                                    18

<210> SEQ ID NO 8
<211> LENGTH: 36
<212> TYPE: DNA
<213> ORGANISM: Artificial Sequence
<220> FEATURE:
<223> OTHER INFORMATION: Oligonucleotide Lb5' Bam HI

<400> SEQUENCE: 8
aaaggatccg cgaacaaacg cccggcgtgg atcatg                                36

<210> SEQ ID NO 9
<211> LENGTH: 27
<212> TYPE: DNA
<213> ORGANISM: Artificial Sequence
<220> FEATURE:
<223> OTHER INFORMATION: Oligonucleotide Lb 3' Sal I

<400> SEQUENCE: 9
gggggtcgac ttaattcttg aatgttc                                          27

<210> SEQ ID NO 10
<211> LENGTH: 837
<212> TYPE: DNA
<213> ORGANISM: Loxosceles boneti
<220> FEATURE:
<223> OTHER INFORMATION: ADNc, clone Lb1

<400> SEQUENCE: 10
```

| | | | | | | | | | | | | | | | | |
|---|---|---|---|---|---|---|---|---|---|---|---|---|---|---|---|---|
| gcg | aac | aaa | cgc | ccg | gcg | tgg | atc | atg | ggc | cac | atg | gtc | aat | gct | att | 48 |
| Ala | Asn | Lys | Arg | Pro | Ala | Trp | Ile | Met | Gly | His | Met | Val | Asn | Ala | Ile | |
| 1 | | | | 5 | | | | | 10 | | | | | 15 | | |
| gct | cag | ata | gac | gag | ttt | gtg | aac | ctt | gga | gcg | aat | tcc | att | gaa | aca | 96 |
| Ala | Gln | Ile | Asp | Glu | Phe | Val | Asn | Leu | Gly | Ala | Asn | Ser | Ile | Glu | Thr | |
| | | | 20 | | | | | 25 | | | | | 30 | | | |
| gac | gtg | tct | ttc | gac | tca | agt | gcc | aat | cct | gaa | tat | acg | tat | cat | ggt | 144 |
| Asp | Val | Ser | Phe | Asp | Ser | Ser | Ala | Asn | Pro | Glu | Tyr | Thr | Tyr | His | Gly | |
| | | 35 | | | | | 40 | | | | | 45 | | | | |
| att | cca | tgt | gat | tgt | gga | agg | act | tgt | acg | aag | tgg | gag | aat | ttc | aac | 192 |
| Ile | Pro | Cys | Asp | Cys | Gly | Arg | Thr | Cys | Thr | Lys | Trp | Glu | Asn | Phe | Asn | |
| 50 | | | | | 55 | | | | | 60 | | | | | | |
| gat | ttt | ctg | gta | gga | ctg | cga | aag | gcc | aca | aca | cca | gac | gac | tcc | aac | 240 |
| Asp | Phe | Leu | Val | Gly | Leu | Arg | Lys | Ala | Thr | Thr | Pro | Asp | Asp | Ser | Asn | |
| 65 | | | | 70 | | | | | 75 | | | | | 80 | | |
| tat | cat | gaa | aag | ttg | att | tta | gtt | gta | ttt | gac | ctg | aaa | acc | ggt | agc | 288 |
| Tyr | His | Glu | Lys | Leu | Ile | Leu | Val | Val | Phe | Asp | Leu | Lys | Thr | Gly | Ser | |
| | | | 85 | | | | | 90 | | | | | 95 | | | |
| ctc | tac | gat | aac | caa | gct | tac | gac | gct | ggg | aag | aaa | tta | gcg | aaa | agt | 336 |
| Leu | Tyr | Asp | Asn | Gln | Ala | Tyr | Asp | Ala | Gly | Lys | Lys | Leu | Ala | Lys | Ser | |
| | | 100 | | | | | 105 | | | | | 110 | | | | |
| ata | ctt | cag | cat | tac | tgg | aac | aac | ggc | aat | aat | ggt | gga | aga | gca | tac | 384 |
| Ile | Leu | Gln | His | Tyr | Trp | Asn | Asn | Gly | Asn | Asn | Gly | Gly | Arg | Ala | Tyr | |
| | | | 115 | | | | | 120 | | | | | 125 | | | |
| att | gta | tta | tcc | ata | cca | aac | ctt | gcc | cat | tat | aaa | tta | att | act | gga | 432 |
| Ile | Val | Leu | Ser | Ile | Pro | Asn | Leu | Ala | His | Tyr | Lys | Leu | Ile | Thr | Gly | |
| 130 | | | | | 135 | | | | | 140 | | | | | | |
| ttt | aaa | gaa | acg | ctc | aca | agc | gat | ggg | cat | cca | gag | ttg | atg | gac | aaa | 480 |
| Phe | Lys | Glu | Thr | Leu | Thr | Ser | Asp | Gly | His | Pro | Glu | Leu | Met | Asp | Lys | |
| 145 | | | | 150 | | | | | 155 | | | | | 160 | | |
| att | gga | tat | gac | ttc | tct | gga | aac | gat | gcc | atc | ggc | gac | gtt | gca | agt | 528 |
| Ile | Gly | Tyr | Asp | Phe | Ser | Gly | Asn | Asp | Ala | Ile | Gly | Asp | Val | Ala | Ser | |
| | | | 165 | | | | | 170 | | | | | 175 | | | |

-continued

```
gct tac cag aaa gcc gga gta aca gga cat gtg tgg cag agc gat ggc      576
Ala Tyr Gln Lys Ala Gly Val Thr Gly His Val Trp Gln Ser Asp Gly
        180                 185                 190 atc acc aac tgt tta ctg cgc gga ctt agt cgc gtg agg gaa gcg gtc      624
Ile Thr Asn Cys Leu Leu Arg Gly Leu Ser Arg Val Arg Glu Ala Val
195                 200                 205 gca aac aga gat tct tcc aac gga tac att aac aaa gtg tac tat tgg      672
Ala Asn Arg Asp Ser Ser Asn Gly Tyr Ile Asn Lys Val Tyr Tyr Trp
210                 215                 220 aca gtg gac aag cgc gca tcg act aga gat gca ctc gat gct gga gtc      720
Thr Val Asp Lys Arg Ala Ser Thr Arg Asp Ala Leu Asp Ala Gly Val
225                 230                 235                 240 gat gga ata atg acc aat tac cca gat gtt att gct gat gtc ctc agt      768
Asp Gly Ile Met Thr Asn Tyr Pro Asp Val Ile Ala Asp Val Leu Ser
                245                 250                 255 gaa tct gct tat agt gcg aaa ttc aga att gcc aca tac gac gac aat      816
Glu Ser Ala Tyr Ser Ala Lys Phe Arg Ile Ala Thr Tyr Asp Asp Asn
            260                 265                 270 cct tgg gaa aca ttc aag aat                                          837
Pro Trp Glu Thr Phe Lys Asn
        275

<210> SEQ ID NO 11
<211> LENGTH: 279
<212> TYPE: PRT
<213> ORGANISM: Loxosceles boneti
<220> FEATURE:
<223> OTHER INFORMATION: Protein SMDrLb, with Sphingomyelinase D and
      dermonecrotic activities.

<400> SEQUENCE: 11

Ala Asn Lys Arg Pro Ala Trp Ile Met Gly His Met Val Asn Ala Ile
1               5                   10                  15

Ala Gln Ile Asp Glu Phe Val Asn Leu Gly Ala Asn Ser Ile Glu Thr
            20                  25                  30

Asp Val Ser Phe Asp Ser Ser Ala Asn Pro Glu Tyr Thr Tyr His Gly
        35                  40                  45

Ile Pro Cys Asp Cys Gly Arg Thr Cys Thr Lys Trp Glu Asn Phe Asn
    50                  55                  60

Asp Phe Leu Val Gly Leu Arg Lys Ala Thr Thr Pro Asp Asp Ser Asn
65                  70                  75                  80

Tyr His Glu Lys Leu Ile Leu Val Val Phe Asp Leu Lys Thr Gly Ser
                85                  90                  95

Leu Tyr Asp Asn Gln Ala Tyr Asp Ala Gly Lys Lys Leu Ala Lys Ser
            100                 105                 110

Ile Leu Gln His Tyr Trp Asn Asn Gly Asn Asn Gly Gly Arg Ala Tyr
        115                 120                 125

Ile Val Leu Ser Ile Pro Asn Leu Ala His Tyr Lys Leu Ile Thr Gly
    130                 135                 140

Phe Lys Glu Thr Leu Thr Ser Asp Gly His Pro Glu Leu Met Asp Lys
145                 150                 155                 160

Ile Gly Tyr Asp Phe Ser Gly Asn Asp Ala Ile Gly Asp Val Ala Ser
                165                 170                 175

Ala Tyr Gln Lys Ala Gly Val Thr Gly His Val Trp Gln Ser Asp Gly
            180                 185                 190

Ile Thr Asn Cys Leu Leu Arg Gly Leu Ser Arg Val Arg Glu Ala Val
        195                 200                 205

Ala Asn Arg Asp Ser Ser Asn Gly Tyr Ile Asn Lys Val Tyr Tyr Trp
```

```
                    210                 215                 220
Thr Val Asp Lys Arg Ala Ser Thr Arg Asp Ala Leu Asp Ala Gly Val
225                 230                 235                 240

Asp Gly Ile Met Thr Asn Tyr Pro Asp Val Ile Ala Asp Val Leu Ser
            245                 250                 255

Glu Ser Ala Tyr Ser Ala Lys Phe Arg Ile Ala Thr Tyr Asp Asp Asn
            260                 265                 270

Pro Trp Glu Thr Phe Lys Asn
        275

<210> SEQ ID NO 12
<211> LENGTH: 837
<212> TYPE: DNA
<213> ORGANISM: Loxosceles reclusa
<220> FEATURE:
<223> OTHER INFORMATION: ADNc, clone Lr1

<400> SEQUENCE: 12 gcg aac aaa cgc ccg gcg tgg atc atg ggg cac atg gtc aac gct att      48
Ala Asn Lys Arg Pro Ala Trp Ile Met Gly His Met Val Asn Ala Ile
1               5                   10                  15 tat cag ata gac gag ttt gtg aac ctt gga gcg aat tcc att gaa aca      96
Tyr Gln Ile Asp Glu Phe Val Asn Leu Gly Ala Asn Ser Ile Glu Thr
                20                  25                  30 gac gtg tct ttc gac aaa gat gcc aat cct gaa tac acg tat cac ggc     144
Asp Val Ser Phe Asp Lys Asp Ala Asn Pro Glu Tyr Thr Tyr His Gly
            35                  40                  45 gtt cca tgt gat tgc ggg agg tct tgc ttg aag tgg gag tat ttt agc     192
Val Pro Cys Asp Cys Gly Arg Ser Cys Leu Lys Trp Glu Tyr Phe Ser
        50                  55                  60 gat ttt cta aaa ggt cta cga aaa gcc aca aca cca ggc gat tcc aag     240
Asp Phe Leu Lys Gly Leu Arg Lys Ala Thr Thr Pro Gly Asp Ser Lys
65                  70                  75                  80 tat cat gca aaa tta gtg tta gtt gta ttt gac ctg aaa acc ggc agc     288
Tyr His Ala Lys Leu Val Leu Val Val Phe Asp Leu Lys Thr Gly Ser
                85                  90                  95 ctc tac gat aac caa gct tac gac gca gga aag aag tta gcg aaa aat     336
Leu Tyr Asp Asn Gln Ala Tyr Asp Ala Gly Lys Lys Leu Ala Lys Asn
            100                 105                 110 ctg ctt aag cat tac tgg aac aac ggc aat aat ggt gga aga gca tac     384
Leu Leu Lys His Tyr Trp Asn Asn Gly Asn Asn Gly Gly Arg Ala Tyr
        115                 120                 125 att gta tta tcc ata cca gac ctt aac cat tat aaa tta att act gga     432
Ile Val Leu Ser Ile Pro Asp Leu Asn His Tyr Lys Leu Ile Thr Gly
130                 135                 140 ttt aaa gaa acg ctc aaa agc gag ggg cat ccc gag tta atg gac aaa     480
Phe Lys Glu Thr Leu Lys Ser Glu Gly His Pro Glu Leu Met Asp Lys
145                 150                 155                 160 gtt gga cat gac ttc tct gga aac gat gcc atc ggc gac gtc ggg aat     528
Val Gly His Asp Phe Ser Gly Asn Asp Ala Ile Gly Asp Val Gly Asn
                165                 170                 175 gct tac aag aaa gcc gga gta aca gga cat gtg tgg cag agc gat ggc     576
Ala Tyr Lys Lys Ala Gly Val Thr Gly His Val Trp Gln Ser Asp Gly
            180                 185                 190 atc acc aac tgt tta ctg cgg gga ctt agt cgt gtg aag gat gct gtg     624
Ile Thr Asn Cys Leu Leu Arg Gly Leu Ser Arg Val Lys Asp Ala Val
        195                 200                 205 aaa aac aga gat tct tca aac gga ttc att aac aaa gtg tac tat tgg     672
Lys Asn Arg Asp Ser Ser Asn Gly Phe Ile Asn Lys Val Tyr Tyr Trp
210                 215                 220
```

```
aca gtg gac aag cgc gca acg act aga gag gca ctc gat gct gga gtc    720
Thr Val Asp Lys Arg Ala Thr Thr Arg Glu Ala Leu Asp Ala Gly Val
225                 230                 235                 240 gat ggc gtg atg acc aat tac ccg gat gtt att act gat gtt ctc aac    768
Asp Gly Val Met Thr Asn Tyr Pro Asp Val Ile Thr Asp Val Leu Asn
                245                 250                 255 gaa tct gct tat aag gcg aaa ttc aga att gcc aca tac gac gac aat    816
Glu Ser Ala Tyr Lys Ala Lys Phe Arg Ile Ala Thr Tyr Asp Asp Asn
            260                 265                 270 cct tgg gaa aca ttc aag aat                                        837
Pro Trp Glu Thr Phe Lys Asn
            275
```

<210> SEQ ID NO 13
<211> LENGTH: 279
<212> TYPE: PRT
<213> ORGANISM: Loxosceles reclusa
<220> FEATURE:
<223> OTHER INFORMATION: Protein SMDrLr1, with Sphingomyelinase D and dermonecrotic activities.

<400> SEQUENCE: 13

```
Ala Asn Lys Arg Pro Ala Trp Ile Met Gly His Met Val Asn Ala Ile
1               5                   10                  15

Tyr Gln Ile Asp Glu Phe Val Asn Leu Gly Ala Asn Ser Ile Glu Thr
            20                  25                  30

Asp Val Ser Phe Asp Lys Asp Ala Asn Pro Glu Tyr Thr Tyr His Gly
        35                  40                  45

Val Pro Cys Asp Cys Gly Arg Ser Cys Leu Lys Trp Glu Tyr Phe Ser
    50                  55                  60

Asp Phe Leu Lys Gly Leu Arg Lys Ala Thr Thr Pro Gly Asp Ser Lys
65                  70                  75                  80

Tyr His Ala Lys Leu Val Leu Val Phe Asp Leu Lys Thr Gly Ser
                85                  90                  95

Leu Tyr Asp Asn Gln Ala Tyr Asp Ala Gly Lys Lys Leu Ala Lys Asn
            100                 105                 110

Leu Leu Lys His Tyr Trp Asn Asn Gly Asn Gly Gly Arg Ala Tyr
        115                 120                 125

Ile Val Leu Ser Ile Pro Asp Leu Asn His Tyr Lys Leu Ile Thr Gly
    130                 135                 140

Phe Lys Glu Thr Leu Lys Ser Glu Gly His Pro Glu Leu Met Asp Lys
145                 150                 155                 160

Val Gly His Asp Phe Ser Gly Asn Asp Ala Ile Gly Asp Val Gly Asn
                165                 170                 175

Ala Tyr Lys Lys Ala Gly Val Thr Gly His Val Trp Gln Ser Asp Gly
            180                 185                 190

Ile Thr Asn Cys Leu Leu Arg Gly Leu Ser Arg Val Lys Asp Ala Val
        195                 200                 205

Lys Asn Arg Asp Ser Ser Asn Gly Phe Ile Asn Lys Val Tyr Tyr Trp
    210                 215                 220

Thr Val Asp Lys Arg Ala Thr Thr Arg Glu Ala Leu Asp Ala Gly Val
225                 230                 235                 240

Asp Gly Val Met Thr Asn Tyr Pro Asp Val Ile Thr Asp Val Leu Asn
                245                 250                 255

Glu Ser Ala Tyr Lys Ala Lys Phe Arg Ile Ala Thr Tyr Asp Asp Asn
            260                 265                 270

Pro Trp Glu Thr Phe Lys Asn
            275
```

<210> SEQ ID NO 14
<211> LENGTH: 837
<212> TYPE: DNA
<213> ORGANISM: Loxosceles reclusa
<220> FEATURE:
<223> OTHER INFORMATION: ADNc, clone Lr2

<400> SEQUENCE: 14

| | | | | | | | | | | | | | | | | |
|---|---|---|---|---|---|---|---|---|---|---|---|---|---|---|---|---|
| gcg | aac | aaa | cgc | ccg | gcg | tgg | atc | atg | ggg | cac | atg | gtc | aac | gct | att | 48 |
| Ala | Asn | Lys | Arg | Pro | Ala | Trp | Ile | Met | Gly | His | Met | Val | Asn | Ala | Ile | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| tat | cag | ata | gac | gag | ttt | gtg | aac | ctt | gga | gcg | aat | tcc | att | gaa | aca | 96 |
| Tyr | Gln | Ile | Asp | Glu | Phe | Val | Asn | Leu | Gly | Ala | Asn | Ser | Ile | Glu | Thr | |
| | | 20 | | | | | 25 | | | | | 30 | | | | |

| | | | | | | | | | | | | | | | | |
|---|---|---|---|---|---|---|---|---|---|---|---|---|---|---|---|---|
| gac | gtg | tct | ttc | gac | aaa | gat | gcc | aat | cct | gaa | tac | acg | tat | cac | ggc | 144 |
| Asp | Val | Ser | Phe | Asp | Lys | Asp | Ala | Asn | Pro | Glu | Tyr | Thr | Tyr | His | Gly | |
| | | | 35 | | | | | 40 | | | | | 45 | | | |

| | | | | | | | | | | | | | | | | |
|---|---|---|---|---|---|---|---|---|---|---|---|---|---|---|---|---|
| gtt | cca | tgt | gat | tgc | ggg | agg | tct | tgc | ttg | aag | tgg | gag | tat | ttt | agc | 192 |
| Val | Pro | Cys | Asp | Cys | Gly | Arg | Ser | Cys | Leu | Lys | Trp | Glu | Tyr | Phe | Ser | |
| | 50 | | | | | 55 | | | | | 60 | | | | | |

| | | | | | | | | | | | | | | | | |
|---|---|---|---|---|---|---|---|---|---|---|---|---|---|---|---|---|
| gat | ttt | cta | aaa | ggt | cta | cga | aaa | gcc | aca | aca | cca | ggc | gat | tcc | aag | 240 |
| Asp | Phe | Leu | Lys | Gly | Leu | Arg | Lys | Ala | Thr | Thr | Pro | Gly | Asp | Ser | Lys | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| tat | cat | gca | aaa | tta | gtg | tta | gtt | gta | ttt | gac | ctg | aaa | acc | ggc | agc | 288 |
| Tyr | His | Ala | Lys | Leu | Val | Leu | Val | Val | Phe | Asp | Leu | Lys | Thr | Gly | Ser | |
| | | | | 85 | | | | | 90 | | | | | 95 | | |

| | | | | | | | | | | | | | | | | |
|---|---|---|---|---|---|---|---|---|---|---|---|---|---|---|---|---|
| ctc | tac | gat | aac | caa | gct | tac | gac | gca | gga | aag | aag | tta | gcg | aaa | aat | 336 |
| Leu | Tyr | Asp | Asn | Gln | Ala | Tyr | Asp | Ala | Gly | Lys | Lys | Leu | Ala | Lys | Asn | |
| | | | 100 | | | | | 105 | | | | | 110 | | | |

| | | | | | | | | | | | | | | | | |
|---|---|---|---|---|---|---|---|---|---|---|---|---|---|---|---|---|
| ctg | ctt | aag | cat | tac | tgg | aac | aac | ggc | aat | aat | ggt | gga | aga | gca | tac | 384 |
| Leu | Leu | Lys | His | Tyr | Trp | Asn | Asn | Gly | Asn | Asn | Gly | Gly | Arg | Ala | Tyr | |
| | | 115 | | | | | 120 | | | | | 125 | | | | |

| | | | | | | | | | | | | | | | | |
|---|---|---|---|---|---|---|---|---|---|---|---|---|---|---|---|---|
| att | gta | tta | tcc | ata | cca | gac | ctt | aac | cat | tat | aaa | tta | att | act | gga | 432 |
| Ile | Val | Leu | Ser | Ile | Pro | Asp | Leu | Asn | His | Tyr | Lys | Leu | Ile | Thr | Gly | |
| | 130 | | | | | 135 | | | | | 140 | | | | | |

| | | | | | | | | | | | | | | | | |
|---|---|---|---|---|---|---|---|---|---|---|---|---|---|---|---|---|
| ttt | aaa | gaa | acg | ctc | aaa | agc | gag | ggg | cat | ccc | gag | tta | atg | gac | aaa | 480 |
| Phe | Lys | Glu | Thr | Leu | Lys | Ser | Glu | Gly | His | Pro | Glu | Leu | Met | Asp | Lys | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| gtt | gga | cat | gac | ttc | tct | gga | aac | gat | gcc | atc | ggc | gac | gtc | ggg | aat | 528 |
| Val | Gly | His | Asp | Phe | Ser | Gly | Asn | Asp | Ala | Ile | Gly | Asp | Val | Gly | Asn | |
| | | | | 165 | | | | | 170 | | | | | 175 | | |

| | | | | | | | | | | | | | | | | |
|---|---|---|---|---|---|---|---|---|---|---|---|---|---|---|---|---|
| gct | tac | aag | aaa | gcc | gga | gta | aca | gga | cat | gtg | tgg | cag | agc | gat | ggc | 576 |
| Ala | Tyr | Lys | Lys | Ala | Gly | Val | Thr | Gly | His | Val | Trp | Gln | Ser | Asp | Gly | |
| | | | 180 | | | | | 185 | | | | | 190 | | | |

| | | | | | | | | | | | | | | | | |
|---|---|---|---|---|---|---|---|---|---|---|---|---|---|---|---|---|
| atc | acc | aac | tgt | tta | ctg | cgg | gga | ctt | agt | cgt | gtg | aag | gat | gct | gtg | 624 |
| Ile | Thr | Asn | Cys | Leu | Leu | Arg | Gly | Leu | Ser | Arg | Val | Lys | Asp | Ala | Val | |
| | | 195 | | | | | 200 | | | | | 205 | | | | |

| | | | | | | | | | | | | | | | | |
|---|---|---|---|---|---|---|---|---|---|---|---|---|---|---|---|---|
| aaa | aac | aga | gat | tct | tca | aac | gga | ttc | att | aac | aaa | gtg | tac | tat | tgg | 672 |
| Lys | Asn | Arg | Asp | Ser | Ser | Asn | Gly | Phe | Ile | Asn | Lys | Val | Tyr | Tyr | Trp | |
| | 210 | | | | | 215 | | | | | 220 | | | | | |

| | | | | | | | | | | | | | | | | |
|---|---|---|---|---|---|---|---|---|---|---|---|---|---|---|---|---|
| aca | gtg | gac | aag | cgc | gca | acg | act | aga | gag | gca | ctc | gat | gct | gga | gtc | 720 |
| Thr | Val | Asp | Lys | Arg | Ala | Thr | Thr | Arg | Glu | Ala | Leu | Asp | Ala | Gly | Val | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| gat | ggc | gtg | atg | acc | aat | tac | ccg | gat | gtt | att | act | gat | gtt | ctc | aac | 768 |
| Asp | Gly | Val | Met | Thr | Asn | Tyr | Pro | Asp | Val | Ile | Thr | Asp | Val | Leu | Asn | |
| | | | | 245 | | | | | 250 | | | | | 255 | | |

| | | | | | | | | | | | | | | | | |
|---|---|---|---|---|---|---|---|---|---|---|---|---|---|---|---|---|
| gaa | tct | gct | tat | aag | gcg | aaa | ttc | aga | att | gcc | aca | tac | gac | gac | aat | 816 |
| Glu | Ser | Ala | Tyr | Lys | Ala | Lys | Phe | Arg | Ile | Ala | Thr | Tyr | Asp | Asp | Asn | |
| | | | 260 | | | | | 265 | | | | | 270 | | | |

| | | | | | | |
|---|---|---|---|---|---|---|
| cct | tgg | gaa | aca | ttc | aag | aat | 837 |

```
Pro Trp Glu Thr Phe Lys Asn
            275

<210> SEQ ID NO 15
<211> LENGTH: 279
<212> TYPE: PRT
<213> ORGANISM: Loxosceles reclusa
<220> FEATURE:
<223> OTHER INFORMATION: Protein SMDrLr2, with Sphingomyelinase D and
      dermonecrotic activities.

<400> SEQUENCE: 15

Ala Asn Lys Arg Pro Ala Trp Ile Met Gly His Met Val Asn Ala Ile
1               5                   10                  15

Tyr Gln Ile Asp Glu Phe Val Asn Leu Gly Ala Asn Ser Ile Glu Thr
            20                  25                  30

Asp Val Ser Phe Asp Lys Asp Ala Asn Pro Glu Tyr Thr Tyr His Gly
        35                  40                  45

Val Pro Cys Asp Cys Gly Arg Ser Cys Leu Lys Trp Glu Tyr Phe Ser
    50                  55                  60

Asp Phe Leu Lys Gly Leu Arg Lys Ala Thr Thr Pro Gly Asp Ser Lys
65                  70                  75                  80

Tyr His Ala Lys Leu Val Leu Val Phe Asp Leu Lys Thr Gly Ser
                85                  90                  95

Leu Tyr Asp Asn Gln Ala Tyr Asp Ala Gly Lys Lys Leu Ala Lys Asn
            100                 105                 110

Leu Leu Lys His Tyr Trp Asn Asn Gly Asn Gly Gly Arg Ala Tyr
        115                 120                 125

Ile Val Leu Ser Ile Pro Asp Leu Asn His Tyr Lys Leu Ile Thr Gly
    130                 135                 140

Phe Lys Glu Thr Leu Lys Ser Glu Gly His Pro Glu Leu Met Asp Lys
145                 150                 155                 160

Val Gly His Asp Phe Ser Gly Asn Asp Ala Ile Gly Asp Val Gly Asn
                165                 170                 175

Ala Tyr Lys Lys Ala Gly Val Thr Gly His Val Trp Gln Ser Asp Gly
            180                 185                 190

Ile Thr Asn Cys Leu Leu Arg Gly Leu Ser Arg Val Lys Asp Ala Val
        195                 200                 205

Lys Asn Arg Asp Ser Ser Asn Gly Phe Ile Asn Lys Val Tyr Tyr Trp
    210                 215                 220

Thr Val Asp Lys Arg Ala Thr Thr Arg Glu Ala Leu Asp Ala Gly Val
225                 230                 235                 240

Asp Gly Val Met Thr Asn Tyr Pro Asp Val Ile Thr Asp Val Leu Asn
                245                 250                 255

Glu Ser Ala Tyr Lys Ala Lys Phe Arg Ile Ala Thr Tyr Asp Asp Asn
            260                 265                 270

Pro Trp Glu Thr Phe Lys Asn
        275

<210> SEQ ID NO 16
<211> LENGTH: 26
<212> TYPE: DNA
<213> ORGANISM: Artificial Sequence
<220> FEATURE:
<223> OTHER INFORMATION: Oligonucleotide L15' BamH I

<400> SEQUENCE: 16
aaaggatccg ctgataaccg tcgtcc                                          26
```

-continued

<210> SEQ ID NO 17
<211> LENGTH: 31
<212> TYPE: DNA
<213> ORGANISM: Artificial Sequence
<220> FEATURE:
<223> OTHER INFORMATION: Oligonucleotide Ll3' Sal I

<400> SEQUENCE: 17 ggggtcgac ctaatttta aaagtctccc a                              31

<210> SEQ ID NO 18
<211> LENGTH: 855
<212> TYPE: DNA
<213> ORGANISM: Loxosceles laeta
<220> FEATURE:
<223> OTHER INFORMATION: ADNc clone Ll1

<400> SEQUENCE: 18

```
gct gat aac cgt cgt cca att tgg aac ctg gct cat atg gtg aac gct      48
Ala Asp Asn Arg Arg Pro Ile Trp Asn Leu Ala His Met Val Asn Ala
1               5                   10                  15 gta gca cag ata cca tcc ttt ttg gat ctt ggt gca aac gca tta gaa      96
Val Ala Gln Ile Pro Ser Phe Leu Asp Leu Gly Ala Asn Ala Leu Glu
            20                  25                  30 gcg gat gtt act ttt aag gga tcg gtg cct acc tac act tac cac gga    144
Ala Asp Val Thr Phe Lys Gly Ser Val Pro Thr Tyr Thr Tyr His Gly
        35                  40                  45 acg cct tgc gac ttc ggt agg gac tgc atc aga tgg gag tat ttc aat    192
Thr Pro Cys Asp Phe Gly Arg Asp Cys Ile Arg Trp Glu Tyr Phe Asn
    50                  55                  60 gta ttt ctg aaa aca ctg aaa gaa tac aca acg cca gga aat gcc aag    240
Val Phe Leu Lys Thr Leu Lys Glu Tyr Thr Thr Pro Gly Asn Ala Lys
65                  70                  75                  80 tat cgt gat ggg ttc ata ctg ttc gtt ttg gac ttg aag acg ggt agc    288
Tyr Arg Asp Gly Phe Ile Leu Phe Val Leu Asp Leu Lys Thr Gly Ser
                85                  90                  95 ctg agc aac gat caa gta cgt cct gcc gga gaa aat gta gca aag gaa    336
Leu Ser Asn Asp Gln Val Arg Pro Ala Gly Glu Asn Val Ala Lys Glu
            100                 105                 110 ctt cta cag aat tac tgg aac aat ggt aat aat ggt gga aga gcg tac    384
Leu Leu Gln Asn Tyr Trp Asn Asn Gly Asn Asn Gly Gly Arg Ala Tyr
        115                 120                 125 gta gta ttg tca tta cct gat atc ggg cat tac gaa ttt gta aga gga    432
Val Val Leu Ser Leu Pro Asp Ile Gly His Tyr Glu Phe Val Arg Gly
    130                 135                 140 ttt aaa gaa gta ctt aag aaa gaa ggt cat gag gac ttg ttg gag aaa    480
Phe Lys Glu Val Leu Lys Lys Glu Gly His Glu Asp Leu Leu Glu Lys
145                 150                 155                 160 gta gga tac gac ttc tct ggc cca tac ctg ccg agc ctt ccc aca cta    528
Val Gly Tyr Asp Phe Ser Gly Pro Tyr Leu Pro Ser Leu Pro Thr Leu
                165                 170                 175 gat gca acc cac gaa gcc tat aaa aaa gct gga gtg gac ggt cac atc    576
Asp Ala Thr His Glu Ala Tyr Lys Lys Ala Gly Val Asp Gly His Ile
            180                 185                 190 tgg tta agt gat ggc ctc acc aat ttt tcc cca ctt ggt gac atg gct    624
Trp Leu Ser Asp Gly Leu Thr Asn Phe Ser Pro Leu Gly Asp Met Ala
        195                 200                 205 cga cta aaa gaa gct ata aaa agt agg gat tcg gca aat gga ttt atc    672
Arg Leu Lys Glu Ala Ile Lys Ser Arg Asp Ser Ala Asn Gly Phe Ile
    210                 215                 220 aat aaa att tac tac tgg tct gtg gac aaa gtg tca aca acg aag gca    720
Asn Lys Ile Tyr Tyr Trp Ser Val Asp Lys Val Ser Thr Thr Lys Ala
```

```
            225                 230                 235                 240
gca ctc gat gtt ggc gtt gat gga ata atg acc aat cat ccg aac gtt       768
Ala Leu Asp Val Gly Val Asp Gly Ile Met Thr Asn His Pro Asn Val
                245                 250                 255 ctt att ggc gtc ctc aag gaa aat gga tac aat gat aag tac aga ttg       816
Leu Ile Gly Val Leu Lys Glu Asn Gly Tyr Asn Asp Lys Tyr Arg Leu
            260                 265                 270 gca act tac gac gac aat cca tgg gag act ttt aaa aat                   855
Ala Thr Tyr Asp Asp Asn Pro Trp Glu Thr Phe Lys Asn
        275                 280                 285

<210> SEQ ID NO 19
<211> LENGTH: 285
<212> TYPE: PRT
<213> ORGANISM: Loxosceles laeta
<220> FEATURE:
<223> OTHER INFORMATION: Protein SMDrLl1, with Sphingomyelinase D and
      dermonecrotic activities.

<400> SEQUENCE: 19

Ala Asp Asn Arg Arg Pro Ile Trp Asn Leu Ala His Met Val Asn Ala
1               5                   10                  15

Val Ala Gln Ile Pro Ser Phe Leu Asp Leu Gly Ala Asn Ala Leu Glu
            20                  25                  30

Ala Asp Val Thr Phe Lys Gly Ser Val Pro Thr Tyr Thr Tyr His Gly
        35                  40                  45

Thr Pro Cys Asp Phe Gly Arg Asp Cys Ile Arg Trp Glu Tyr Phe Asn
    50                  55                  60

Val Phe Leu Lys Thr Leu Lys Glu Tyr Thr Thr Pro Gly Asn Ala Lys
65                  70                  75                  80

Tyr Arg Asp Gly Phe Ile Leu Phe Val Leu Asp Leu Lys Thr Gly Ser
                85                  90                  95

Leu Ser Asn Asp Gln Val Arg Pro Ala Gly Glu Asn Val Ala Lys Glu
            100                 105                 110

Leu Leu Gln Asn Tyr Trp Asn Asn Gly Asn Asn Gly Gly Arg Ala Tyr
        115                 120                 125

Val Val Leu Ser Leu Pro Asp Ile Gly His Tyr Glu Phe Val Arg Gly
    130                 135                 140

Phe Lys Glu Val Leu Lys Lys Glu Gly His Glu Asp Leu Leu Glu Lys
145                 150                 155                 160

Val Gly Tyr Asp Phe Ser Gly Pro Tyr Leu Pro Ser Leu Pro Thr Leu
                165                 170                 175

Asp Ala Thr His Glu Ala Tyr Lys Lys Ala Gly Val Asp Gly His Ile
            180                 185                 190

Trp Leu Ser Asp Gly Leu Thr Asn Phe Ser Pro Leu Gly Asp Met Ala
        195                 200                 205

Arg Leu Lys Glu Ala Ile Lys Ser Arg Asp Ser Ala Asn Gly Phe Ile
    210                 215                 220

Asn Lys Ile Tyr Tyr Trp Ser Val Asp Lys Val Ser Thr Thr Lys Ala
225                 230                 235                 240

Ala Leu Asp Val Gly Val Asp Gly Ile Met Thr Asn His Pro Asn Val
                245                 250                 255

Leu Ile Gly Val Leu Lys Glu Asn Gly Tyr Asn Asp Lys Tyr Arg Leu
            260                 265                 270

Ala Thr Tyr Asp Asp Asn Pro Trp Glu Thr Phe Lys Asn
        275                 280                 285
```

<210> SEQ ID NO 20
<211> LENGTH: 855
<212> TYPE: DNA
<213> ORGANISM: Loxosceles laeta
<220> FEATURE:
<223> OTHER INFORMATION: ADNc clone Ll2

<400> SEQUENCE: 20

| | | | | | | | | | | | | | | | | |
|---|---|---|---|---|---|---|---|---|---|---|---|---|---|---|---|---|
| gct | gat | aac | cgt | cgt | cca | att | tgg | aac | ctg | ggc | cac | atg | gtg | aac | gct | 48 |
| Ala | Asp | Asn | Arg | Arg | Pro | Ile | Trp | Asn | Leu | Gly | His | Met | Val | Asn | Ala | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| gta | aaa | cag | ata | cca | act | ttt | tta | aat | gat | ggt | gca | aac | gca | ata | gaa | 96 |
| Val | Lys | Gln | Ile | Pro | Thr | Phe | Leu | Asn | Asp | Gly | Ala | Asn | Ala | Ile | Glu | |
| | | | 20 | | | | | 25 | | | | | 30 | | | |

| | | | | | | | | | | | | | | | | |
|---|---|---|---|---|---|---|---|---|---|---|---|---|---|---|---|---|
| gcg | gac | att | act | ttt | aag | gga | gcg | gtg | ccc | acc | tac | agt | tac | cat | gga | 144 |
| Ala | Asp | Ile | Thr | Phe | Lys | Gly | Ala | Val | Pro | Thr | Tyr | Ser | Tyr | His | Gly | |
| | | 35 | | | | | 40 | | | | | 45 | | | | |

| | | | | | | | | | | | | | | | | |
|---|---|---|---|---|---|---|---|---|---|---|---|---|---|---|---|---|
| acg | cct | tgc | gac | ttc | ggc | agg | gat | tgc | atc | aga | tgg | gag | tat | ttt | gac | 192 |
| Thr | Pro | Cys | Asp | Phe | Gly | Arg | Asp | Cys | Ile | Arg | Trp | Glu | Tyr | Phe | Asp | |
| | 50 | | | | | 55 | | | | | 60 | | | | | |

| | | | | | | | | | | | | | | | | |
|---|---|---|---|---|---|---|---|---|---|---|---|---|---|---|---|---|
| gta | ttc | ttg | aga | aca | ctg | aga | gaa | tat | act | acg | cca | gga | aat | tcc | aag | 240 |
| Val | Phe | Leu | Arg | Thr | Leu | Arg | Glu | Tyr | Thr | Thr | Pro | Gly | Asn | Ser | Lys | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| tat | cgt | gag | aag | ttt | ata | ctg | ttt | gtt | ttg | gac | ttg | aag | acg | ggc | agc | 288 |
| Tyr | Arg | Glu | Lys | Phe | Ile | Leu | Phe | Val | Leu | Asp | Leu | Lys | Thr | Gly | Ser | |
| | | | | 85 | | | | | 90 | | | | | 95 | | |

| | | | | | | | | | | | | | | | | |
|---|---|---|---|---|---|---|---|---|---|---|---|---|---|---|---|---|
| ttg | aac | aac | cat | gaa | gtg | aga | aaa | gcc | gga | gaa | aat | gta | gcc | aag | gga | 336 |
| Leu | Asn | Asn | His | Glu | Val | Arg | Lys | Ala | Gly | Glu | Asn | Val | Ala | Lys | Gly | |
| | | | 100 | | | | | 105 | | | | | 110 | | | |

| | | | | | | | | | | | | | | | | |
|---|---|---|---|---|---|---|---|---|---|---|---|---|---|---|---|---|
| ctt | ctg | gag | aat | tac | tgg | aac | aat | ggt | aat | aat | gga | gga | aga | gca | tac | 384 |
| Leu | Leu | Glu | Asn | Tyr | Trp | Asn | Asn | Gly | Asn | Asn | Gly | Gly | Arg | Ala | Tyr | |
| | | 115 | | | | | 120 | | | | | 125 | | | | |

| | | | | | | | | | | | | | | | | |
|---|---|---|---|---|---|---|---|---|---|---|---|---|---|---|---|---|
| gta | gta | ttg | tca | tta | cct | gat | atc | gcg | cat | tac | gaa | ttt | ata | cga | aca | 432 |
| Val | Val | Leu | Ser | Leu | Pro | Asp | Ile | Ala | His | Tyr | Glu | Phe | Ile | Arg | Thr | |
| | 130 | | | | | 135 | | | | | 140 | | | | | |

| | | | | | | | | | | | | | | | | |
|---|---|---|---|---|---|---|---|---|---|---|---|---|---|---|---|---|
| ttt | aaa | gaa | gta | ctt | aag | aca | gca | ggt | cat | gag | aat | ttg | ttg | gac | aaa | 480 |
| Phe | Lys | Glu | Val | Leu | Lys | Thr | Ala | Gly | His | Glu | Asn | Leu | Leu | Asp | Lys | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| gta | gga | tac | gac | tta | tct | ggc | cca | tac | tgg | cca | agc | cta | ccc | tcg | ctg | 528 |
| Val | Gly | Tyr | Asp | Leu | Ser | Gly | Pro | Tyr | Trp | Pro | Ser | Leu | Pro | Ser | Leu | |
| | | | | 165 | | | | | 170 | | | | | 175 | | |

| | | | | | | | | | | | | | | | | |
|---|---|---|---|---|---|---|---|---|---|---|---|---|---|---|---|---|
| gat | tca | gtt | cac | gaa | gcc | ttt | aaa | aaa | gct | gga | gtg | gat | ggt | cac | gtc | 576 |
| Asp | Ser | Val | His | Glu | Ala | Phe | Lys | Lys | Ala | Gly | Val | Asp | Gly | His | Val | |
| | | | 180 | | | | | 185 | | | | | 190 | | | |

| | | | | | | | | | | | | | | | | |
|---|---|---|---|---|---|---|---|---|---|---|---|---|---|---|---|---|
| tgg | cta | agt | gat | ggc | ctc | act | aat | tgg | gcg | aaa | ctt | ggt | gac | atg | gct | 624 |
| Trp | Leu | Ser | Asp | Gly | Leu | Thr | Asn | Trp | Ala | Lys | Leu | Gly | Asp | Met | Ala | |
| | | 195 | | | | | 200 | | | | | 205 | | | | |

| | | | | | | | | | | | | | | | | |
|---|---|---|---|---|---|---|---|---|---|---|---|---|---|---|---|---|
| cga | cta | aaa | gaa | att | ata | aaa | agt | agg | gac | tcg | gaa | aat | gga | ttt | att | 672 |
| Arg | Leu | Lys | Glu | Ile | Ile | Lys | Ser | Arg | Asp | Ser | Glu | Asn | Gly | Phe | Ile | |
| | 210 | | | | | 215 | | | | | 220 | | | | | |

| | | | | | | | | | | | | | | | | |
|---|---|---|---|---|---|---|---|---|---|---|---|---|---|---|---|---|
| agt | aaa | gtt | tac | tac | tgg | tct | gta | gac | aaa | tat | tca | aca | aca | aga | aca | 720 |
| Ser | Lys | Val | Tyr | Tyr | Trp | Ser | Val | Asp | Lys | Tyr | Ser | Thr | Thr | Arg | Thr | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| gca | ctc | gat | gtt | ggc | gtt | gat | gga | ata | atg | acc | aat | tat | ccg | tac | gtt | 768 |
| Ala | Leu | Asp | Val | Gly | Val | Asp | Gly | Ile | Met | Thr | Asn | Tyr | Pro | Tyr | Val | |
| | | | | 245 | | | | | 250 | | | | | 255 | | |

| | | | | | | | | | | | | | | | | |
|---|---|---|---|---|---|---|---|---|---|---|---|---|---|---|---|---|
| att | att | gac | gtc | ctc | aac | gaa | aat | gga | tac | aag | gac | aaa | tac | agg | ttg | 816 |
| Ile | Ile | Asp | Val | Leu | Asn | Glu | Asn | Gly | Tyr | Lys | Asp | Lys | Tyr | Arg | Leu | |
| | | | 260 | | | | | 265 | | | | | 270 | | | |

| | | | | | | | | | | | | |
|---|---|---|---|---|---|---|---|---|---|---|---|---|
| gca | act | tac | gac | gac | aat | cca | tgg | gag | act | ttt | aaa | aat | 855 |
| Ala | Thr | Tyr | Asp | Asp | Asn | Pro | Trp | Glu | Thr | Phe | Lys | Asn | |
| | | 275 | | | | | 280 | | | | | 285 | |

```
<210> SEQ ID NO 21
<211> LENGTH: 285
<212> TYPE: PRT
<213> ORGANISM: Loxosceles laeta
<220> FEATURE:
<223> OTHER INFORMATION: Protein SMDrLl2, with Sphingomyelinase D and
      dermonecrotic activities.

<400> SEQUENCE: 21

Ala Asp Asn Arg Arg Pro Ile Trp Asn Leu Gly His Met Val Asn Ala
1               5                   10                  15

Val Lys Gln Ile Pro Thr Phe Leu Asn Asp Gly Ala Asn Ala Ile Glu
            20                  25                  30

Ala Asp Ile Thr Phe Lys Gly Ala Val Pro Thr Tyr Ser Tyr His Gly
        35                  40                  45

Thr Pro Cys Asp Phe Gly Arg Asp Cys Ile Arg Trp Glu Tyr Phe Asp
    50                  55                  60

Val Phe Leu Arg Thr Leu Arg Glu Tyr Thr Thr Pro Gly Asn Ser Lys
65                  70                  75                  80

Tyr Arg Glu Lys Phe Ile Leu Phe Val Leu Asp Leu Lys Thr Gly Ser
                85                  90                  95

Leu Asn Asn His Glu Val Arg Lys Ala Gly Glu Asn Val Ala Lys Gly
            100                 105                 110

Leu Leu Glu Asn Tyr Trp Asn Gly Asn Asn Gly Gly Arg Ala Tyr
        115                 120                 125

Val Val Leu Ser Leu Pro Asp Ile Ala His Tyr Glu Phe Ile Arg Thr
    130                 135                 140

Phe Lys Glu Val Leu Lys Thr Ala Gly His Glu Asn Leu Leu Asp Lys
145                 150                 155                 160

Val Gly Tyr Asp Leu Ser Gly Pro Tyr Trp Pro Ser Leu Pro Ser Leu
                165                 170                 175

Asp Ser Val His Glu Ala Phe Lys Lys Ala Gly Val Asp Gly His Val
            180                 185                 190

Trp Leu Ser Asp Gly Leu Thr Asn Trp Ala Lys Leu Gly Asp Met Ala
        195                 200                 205

Arg Leu Lys Glu Ile Ile Lys Ser Arg Asp Ser Glu Asn Gly Phe Ile
    210                 215                 220

Ser Lys Val Tyr Tyr Trp Ser Val Asp Lys Tyr Ser Thr Thr Arg Thr
225                 230                 235                 240

Ala Leu Asp Val Gly Val Asp Gly Ile Met Thr Asn Tyr Pro Tyr Val
                245                 250                 255

Ile Ile Asp Val Leu Asn Glu Asn Gly Tyr Lys Asp Lys Tyr Arg Leu
            260                 265                 270

Ala Thr Tyr Asp Asp Asn Pro Trp Glu Thr Phe Lys Asn
        275                 280                 285

<210> SEQ ID NO 22
<211> LENGTH: 24
<212> TYPE: DNA
<213> ORGANISM: Artificial Sequence
<220> FEATURE:
<223> OTHER INFORMATION: Oligonucleotide Lb5' incomplete

<400> SEQUENCE: 22
tttggatccc cggcgtggat catg                                          24

<210> SEQ ID NO 23
```

```
<211> LENGTH: 28
<212> TYPE: DNA
<213> ORGANISM: Artificial Sequence
<220> FEATURE:
<223> OTHER INFORMATION: Oligonucleotide Lb3' Bgl II

<400> SEQUENCE: 23
ggggagatct attcttgaat gtttccca                                              28

<210> SEQ ID NO 24
<211> LENGTH: 30
<212> TYPE: DNA
<213> ORGANISM: Artificial Sequence
<220> FEATURE:
<223> OTHER INFORMATION: Oligonucleotide Ll3' Bgl II

<400> SEQUENCE: 24
ggggagatct attttaaaa gtctcccatg                                             30

<210> SEQ ID NO 25
<211> LENGTH: 12
<212> TYPE: PRT
<213> ORGANISM: Artificial Sequence
<220> FEATURE:
<223> OTHER INFORMATION: Amino term added to the protein by the plasmid
      pQE30

<400> SEQUENCE: 25

Met Arg Gly Ser His His His His His His Gly Ser
1               5                   10

<210> SEQ ID NO 26
<211> LENGTH: 8
<212> TYPE: PRT
<213> ORGANISM: Artificial Sequence
<220> FEATURE:
<223> OTHER INFORMATION: Carboxy term added to the protein by the
      plasmid pQE60

<400> SEQUENCE: 26

Arg Ser His His His His His His
1               5

<210> SEQ ID NO 27
<211> LENGTH: 837
<212> TYPE: DNA
<213> ORGANISM: Loxosceles boneti
<220> FEATURE:
<223> OTHER INFORMATION: ADNc clone Lb1(H11K) codon for Histidine 11 is
      substituted by codon for Lysine

<400> SEQUENCE: 27 gcg aac aaa cgc ccg gcg tgg atc atg ggc aaa atg gtc aat gct att        48
Ala Asn Lys Arg Pro Ala Trp Ile Met Gly Lys Met Val Asn Ala Ile
1               5                   10                  15 gct cag ata gac gag ttt gtg aac ctt gga gcg aat tcc att gaa aca        96
Ala Gln Ile Asp Glu Phe Val Asn Leu Gly Ala Asn Ser Ile Glu Thr
            20                  25                  30 gac gtg tct ttc gac tca agt gcc aat cct gaa tat acg tat cat ggt       144
Asp Val Ser Phe Asp Ser Ser Ala Asn Pro Glu Tyr Thr Tyr His Gly
        35                  40                  45 att cca tgt gat tgt gga agg act tgt acg aag tgg gag aat ttc aac       192
Ile Pro Cys Asp Cys Gly Arg Thr Cys Thr Lys Trp Glu Asn Phe Asn
    50                  55                  60 gat ttt ctg gta gga ctg cga aag gcc aca aca cca gac gac tcc aac       240
Asp Phe Leu Val Gly Leu Arg Lys Ala Thr Thr Pro Asp Asp Ser Asn
65                  70                  75                  80
```

| | | | | | | | | | | | | | | | |
|---|---|---|---|---|---|---|---|---|---|---|---|---|---|---|---|
| tat | cat | gaa | aag | ttg | att | tta | gtt | gta | ttt | gac | ctg | aaa | acc | ggt | agc | 288 |
| Tyr | His | Glu | Lys | Leu | Ile | Leu | Val | Val | Phe | Asp | Leu | Lys | Thr | Gly | Ser |
| | | | 85 | | | | | 90 | | | | | 95 | | |

```
tat cat gaa aag ttg att tta gtt gta ttt gac ctg aaa acc ggt agc        288
Tyr His Glu Lys Leu Ile Leu Val Val Phe Asp Leu Lys Thr Gly Ser
            85                  90                  95 ctc tac gat aac caa gct tac gac gct ggg aag aaa tta gcg aaa agt        336
Leu Tyr Asp Asn Gln Ala Tyr Asp Ala Gly Lys Lys Leu Ala Lys Ser
            100                 105                 110 ata ctt cag cat tac tgg aac aac ggc aat aat ggt gga aga gca tac        384
Ile Leu Gln His Tyr Trp Asn Asn Gly Asn Asn Gly Gly Arg Ala Tyr
            115                 120                 125 att gta tta tcc ata cca aac ctt gcc cat tat aaa tta att act gga        432
Ile Val Leu Ser Ile Pro Asn Leu Ala His Tyr Lys Leu Ile Thr Gly
130                 135                 140 ttt aaa gaa acg ctc aca agc gat ggg cat cca gag ttg atg gac aaa        480
Phe Lys Glu Thr Leu Thr Ser Asp Gly His Pro Glu Leu Met Asp Lys
145                 150                 155                 160 att gga tat gac ttc tct gga aac gat gcc atc ggc gac gtt gca agt        528
Ile Gly Tyr Asp Phe Ser Gly Asn Asp Ala Ile Gly Asp Val Ala Ser
                165                 170                 175 gct tac cag aaa gcc gga gta aca gga cat gtg tgg cag agc gat ggc        576
Ala Tyr Gln Lys Ala Gly Val Thr Gly His Val Trp Gln Ser Asp Gly
            180                 185                 190 atc acc aac tgt tta ctg cgc gga ctt agt cgc gtg agg gaa gcg gtc        624
Ile Thr Asn Cys Leu Leu Arg Gly Leu Ser Arg Val Arg Glu Ala Val
            195                 200                 205 gca aac aga gat tct tcc aac gga tac att aac aaa gtg tac tat tgg        672
Ala Asn Arg Asp Ser Ser Asn Gly Tyr Ile Asn Lys Val Tyr Tyr Trp
210                 215                 220 aca gtg gac aag cgc gca tcg act aga gat gca ctc gat gct gga gtc        720
Thr Val Asp Lys Arg Ala Ser Thr Arg Asp Ala Leu Asp Ala Gly Val
225                 230                 235                 240 gat gga ata atg acc aat tac cca gat gtt att gct gat gtc ctc agt        768
Asp Gly Ile Met Thr Asn Tyr Pro Asp Val Ile Ala Asp Val Leu Ser
                245                 250                 255 gaa tct gct tat agt gcg aaa ttc aga att gcc aca tac gac gac aat        816
Glu Ser Ala Tyr Ser Ala Lys Phe Arg Ile Ala Thr Tyr Asp Asp Asn
            260                 265                 270 cct tgg gaa aca ttc aag aat                                            837
Pro Trp Glu Thr Phe Lys Asn
            275

<210> SEQ ID NO 28
<211> LENGTH: 279
<212> TYPE: PRT
<213> ORGANISM: Loxosceles boneti
<220> FEATURE:
<223> OTHER INFORMATION: Protein SMDrLb (H11K), codon for Histidine 11
      substituted by codon for Lysine, without Sphingomyelinase D and
      dermonecrotic activities but it does generate neutralizing
      antibodies agaist Loxosceles boneti venom.

<400> SEQUENCE: 28

Ala Asn Lys Arg Pro Ala Trp Ile Met Gly Lys Met Val Asn Ala Ile
1               5                   10                  15

Ala Gln Ile Asp Glu Phe Val Asn Leu Gly Ala Asn Ser Ile Glu Thr
            20                  25                  30

Asp Val Ser Phe Asp Ser Ser Ala Asn Pro Glu Tyr Thr Tyr His Gly
        35                  40                  45

Ile Pro Cys Asp Cys Gly Arg Thr Cys Thr Lys Trp Glu Asn Phe Asn
    50                  55                  60

Asp Phe Leu Val Gly Leu Arg Lys Ala Thr Thr Pro Asp Asp Ser Asn
65                  70                  75                  80
```

```
Tyr His Glu Lys Leu Ile Leu Val Val Phe Asp Leu Lys Thr Gly Ser
            85                  90                  95

Leu Tyr Asp Asn Gln Ala Tyr Asp Ala Gly Lys Lys Leu Ala Lys Ser
            100                 105                 110

Ile Leu Gln His Tyr Trp Asn Asn Gly Asn Asn Gly Gly Arg Ala Tyr
            115                 120                 125

Ile Val Leu Ser Ile Pro Asn Leu Ala His Tyr Lys Leu Ile Thr Gly
        130                 135                 140

Phe Lys Glu Thr Leu Thr Ser Asp Gly His Pro Glu Leu Met Asp Lys
145                 150                 155                 160

Ile Gly Tyr Asp Phe Ser Gly Asn Asp Ala Ile Gly Asp Val Ala Ser
                165                 170                 175

Ala Tyr Gln Lys Ala Gly Val Thr Gly His Val Trp Gln Ser Asp Gly
            180                 185                 190

Ile Thr Asn Cys Leu Leu Arg Gly Leu Ser Arg Val Arg Glu Ala Val
            195                 200                 205

Ala Asn Arg Asp Ser Ser Asn Gly Tyr Ile Asn Lys Val Tyr Tyr Trp
        210                 215                 220

Thr Val Asp Lys Arg Ala Ser Thr Arg Asp Ala Leu Asp Ala Gly Val
225                 230                 235                 240

Asp Gly Ile Met Thr Asn Tyr Pro Asp Val Ile Ala Asp Val Leu Ser
                245                 250                 255

Glu Ser Ala Tyr Ser Ala Lys Phe Arg Ile Ala Thr Tyr Asp Asp Asn
            260                 265                 270

Pro Trp Glu Thr Phe Lys Asn
        275

<210> SEQ ID NO 29
<211> LENGTH: 837
<212> TYPE: DNA
<213> ORGANISM: Loxosceles boneti
<220> FEATURE:
<223> OTHER INFORMATION: ADNc clone Lb1(E31K). Codon for Glutamic Acid
      31 substituted by codon for Lysine.

<400> SEQUENCE: 29 gcg aac aaa cgc ccg gcg tgg atc atg ggc cac atg gtc aat gct att      48
Ala Asn Lys Arg Pro Ala Trp Ile Met Gly His Met Val Asn Ala Ile
1               5                   10                  15 gct cag ata gac gag ttt gtg aac ctt gga gcg aat tcc att aaa aca      96
Ala Gln Ile Asp Glu Phe Val Asn Leu Gly Ala Asn Ser Ile Lys Thr
            20                  25                  30 gac gtg tct ttc gac tca agt gcc aat cct gaa tat acg tat cat ggt     144
Asp Val Ser Phe Asp Ser Ser Ala Asn Pro Glu Tyr Thr Tyr His Gly
        35                  40                  45 att cca tgt gat tgt gga agg act tgt acg aag tgg gag aat ttc aac     192
Ile Pro Cys Asp Cys Gly Arg Thr Cys Thr Lys Trp Glu Asn Phe Asn
    50                  55                  60 gat ttt ctg gta gga ctg cga aag gcc aca aca cca gac gac tcc aac     240
Asp Phe Leu Val Gly Leu Arg Lys Ala Thr Thr Pro Asp Asp Ser Asn
65                  70                  75                  80 tat cat gaa aag ttg att tta gtt gta ttt gac ctg aaa acc ggt agc     288
Tyr His Glu Lys Leu Ile Leu Val Val Phe Asp Leu Lys Thr Gly Ser
                85                  90                  95 ctc tac gat aac caa gct tac gac gct ggg aag aaa tta gcg aaa agt     336
Leu Tyr Asp Asn Gln Ala Tyr Asp Ala Gly Lys Lys Leu Ala Lys Ser
            100                 105                 110 ata ctt cag cat tac tgg aac aac ggc aat aat ggt gga aga gca tac     384
```

```
Ile Leu Gln His Tyr Trp Asn Asn Gly Asn Asn Gly Gly Arg Ala Tyr
        115                 120                 125 att gta tta tcc ata cca aac ctt gcc cat tat aaa tta att act gga      432
Ile Val Leu Ser Ile Pro Asn Leu Ala His Tyr Lys Leu Ile Thr Gly
130                 135                 140 ttt aaa gaa acg ctc aca agc gat ggg cat cca gag ttg atg gac aaa      480
Phe Lys Glu Thr Leu Thr Ser Asp Gly His Pro Glu Leu Met Asp Lys
145                 150                 155                 160 att gga tat gac ttc tct gga aac gat gcc atc ggc gac gtt gca agt      528
Ile Gly Tyr Asp Phe Ser Gly Asn Asp Ala Ile Gly Asp Val Ala Ser
                165                 170                 175 gct tac cag aaa gcc gga gta aca gga cat gtg tgg cag agc gat ggc      576
Ala Tyr Gln Lys Ala Gly Val Thr Gly His Val Trp Gln Ser Asp Gly
                180                 185                 190 atc acc aac tgt tta ctg cgc gga ctt agt cgc gtg agg gaa gcg gtc      624
Ile Thr Asn Cys Leu Leu Arg Gly Leu Ser Arg Val Arg Glu Ala Val
                195                 200                 205 gca aac aga gat tct tcc aac gga tac att aac aaa gtg tac tat tgg      672
Ala Asn Arg Asp Ser Ser Asn Gly Tyr Ile Asn Lys Val Tyr Tyr Trp
210                 215                 220 aca gtg gac aag cgc gca tcg act aga gat gca ctc gat gct gga gtc      720
Thr Val Asp Lys Arg Ala Ser Thr Arg Asp Ala Leu Asp Ala Gly Val
225                 230                 235                 240 gat gga ata atg acc aat tac cca gat gtt att gct gat gtc ctc agt      768
Asp Gly Ile Met Thr Asn Tyr Pro Asp Val Ile Ala Asp Val Leu Ser
                245                 250                 255 gaa tct gct tat agt gcg aaa ttc aga att gcc aca tac gac gac aat      816
Glu Ser Ala Tyr Ser Ala Lys Phe Arg Ile Ala Thr Tyr Asp Asp Asn
                260                 265                 270 cct tgg gaa aca ttc aag aat                                          837
Pro Trp Glu Thr Phe Lys Asn
                275

<210> SEQ ID NO 30
<211> LENGTH: 279
<212> TYPE: PRT
<213> ORGANISM: Loxosceles boneti
<220> FEATURE:
<223> OTHER INFORMATION: Protein SMDrLb (E31K), codon for Glumatic acid
      31 substituted by codon for Lysine, without Sphingomyelinase D and
      dermonecrotic activities but it does generate neutralizing
      antibodies agaist Loxosceles boneti venom.

<400> SEQUENCE: 30

Ala Asn Lys Arg Pro Ala Trp Ile Met Gly His Met Val Asn Ala Ile
1               5                   10                  15

Ala Gln Ile Asp Glu Phe Val Asn Leu Gly Ala Asn Ser Ile Lys Thr
            20                  25                  30

Asp Val Ser Phe Asp Ser Ser Ala Asn Pro Glu Tyr Thr Tyr His Gly
        35                  40                  45

Ile Pro Cys Asp Cys Gly Arg Thr Cys Thr Lys Trp Glu Asn Phe Asn
    50                  55                  60

Asp Phe Leu Val Gly Leu Arg Lys Ala Thr Thr Pro Asp Asp Ser Asn
65                  70                  75                  80

Tyr His Glu Lys Leu Ile Leu Val Val Phe Asp Leu Lys Thr Gly Ser
                85                  90                  95

Leu Tyr Asp Asn Gln Ala Tyr Asp Ala Gly Lys Lys Leu Ala Lys Ser
            100                 105                 110

Ile Leu Gln His Tyr Trp Asn Asn Gly Asn Asn Gly Gly Arg Ala Tyr
        115                 120                 125
```

```
Ile Val Leu Ser Ile Pro Asn Leu Ala His Tyr Lys Leu Ile Thr Gly
            130             135             140

Phe Lys Glu Thr Leu Thr Ser Asp Gly His Pro Glu Leu Met Asp Lys
145             150             155                         160

Ile Gly Tyr Asp Phe Ser Gly Asn Asp Ala Ile Gly Asp Val Ala Ser
                165             170             175

Ala Tyr Gln Lys Ala Gly Val Thr Gly His Val Trp Gln Ser Asp Gly
            180             185             190

Ile Thr Asn Cys Leu Leu Arg Gly Leu Ser Arg Val Arg Glu Ala Val
            195             200             205

Ala Asn Arg Asp Ser Ser Asn Gly Tyr Ile Asn Lys Val Tyr Tyr Trp
            210             215             220

Thr Val Asp Lys Arg Ala Ser Thr Arg Asp Ala Leu Asp Ala Gly Val
225             230             235             240

Asp Gly Ile Met Thr Asn Tyr Pro Asp Val Ile Ala Asp Val Leu Ser
                245             250             255

Glu Ser Ala Tyr Ser Ala Lys Phe Arg Ile Ala Thr Tyr Asp Asp Asn
            260             265             270

Pro Trp Glu Thr Phe Lys Asn
            275
```